United States Patent [19]

Hui et al.

[11] Patent Number: 5,554,653
[45] Date of Patent: Sep. 10, 1996

[54] INHIBITORS OF HIV PROTEASE USEFUL FOR THE TREATMENT OF AIDS

[75] Inventors: Kwan Hui, Carmel; Charles D. Jones, Indianapolis; Louis N. Jungheim, Indianapolis; Timothy A. Shepherd, Indianapolis, all of Ind.

[73] Assignee: Eli Lilly and Company, Indianapolis, Ind.

[21] Appl. No.: 995,620

[22] Filed: Dec. 22, 1992

[51] Int. Cl.⁶ ...................... C07D 215/48; C07D 217/26; C07C 321/28; C07C 323/20

[52] U.S. Cl. .......................... 514/605; 514/312; 514/613; 514/619; 514/620; 564/162; 564/85; 564/86; 546/169; 546/156; 546/157

[58] Field of Search ..................... 546/169, 156, 546/157; 435/219, 184; 564/162, 166, 85, 86; 568/63; 514/613, 618, 312, 605, 619, 620

[56] References Cited

U.S. PATENT DOCUMENTS 5,142,056  8/1992  Kempe et al. ........................ 546/264
5,475,136  12/1995  Fritz et al. .......................... 564/162

FOREIGN PATENT DOCUMENTS 0337714  10/1989  European Pat. Off. .
0346847  12/1989  European Pat. Off. .
0361341  4/1990  European Pat. Off. .
0402646  12/1990  European Pat. Off. .

OTHER PUBLICATIONS

Roberts, N. A. et al., Science, 248, 358–361 (1990).
Vara Prasad, J. V. N. et al., Peptides, Chemistry and Biology, Proceedings of the Twelfth American Peptide Symposium, Jun. 16–21, 721–722 (1991).
Thaisrivongs, S. et al., J. Med Chem, 34, 2344–2356 (1991).

Primary Examiner—Michael G. Wityshyn
Assistant Examiner—Francisco C. Prats
Attorney, Agent, or Firm—Janet T. McClain

[57] ABSTRACT

The present invention provides novel HIV protease inhibitors, pharmaceutical formulations containing those compounds and methods of treating and/or preventing HIV infection and/or AIDS.

28 Claims, No Drawings

INHIBITORS OF HIV PROTEASE USEFUL FOR THE TREATMENT OF AIDS

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature vital proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment of AIDS and the prevention or treatment of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, the currently used therapeutic, AZT, is an inhibitor of the viral reverse transcriptase. H. Hitsuya, NS. Broder, "Inhibition of the In Vitro Infectivity in cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known compounds suffer from toxicity problems, lack of bioavailability or short in vivo half-lives. Thus, despite the recognized therapeutic potential associated with a protease inhibitor and the research efforts expended thus far, a viable therapeutic agent has not yet emerged.

Accordingly, a primary object of the present invention is to provide novel HIV protease inhibitors which Are useful in the treatment or prevention of HIV infection and/or the resulting acquired immune deficiency syndrome (AIDS).

A further object of the present invention is to provide therapeutic compositions that are useful in the treatment or prevention of HIV infection and/or AIDS.

Still another object is to provide methods for the treatment or prevention of HIV infection and/or AIDS.

Other objects, features and advantages will become apparent to those skilled in the art from the following description and claims.

SUMMARY OF THE INVENTION

The present invention relates to compounds of formula I, below, and pharmaceutically acceptable salts thereof that inhibit the protease encoded by human immunodeficiency virus (HIV) type 1 (HIV-1) or type 2 (HIV-2). These compounds are useful in the treatment or prevention of HIV infection and the treatment or prevention of the resulting acquired immune deficiency syndrome (AIDS). The compounds, their pharmaceutically acceptable salts, and the pharmaceutical compositions can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method of inhibiting HIV replication in an HIV infected cell, a cell susceptible to HIV infection or a primate in need thereof, thus treating or preventing HIV infection and/or AIDS, comprising administering an effective amount of a compound of formula I

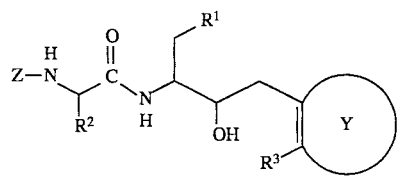

wherein:

Z is hydrogen, formyl, carbamoyl, $C_2$–$C_6$ alkanoyl, $C_1$–$C_4$ alkoxycarbonyl, —C(O)CF$_3$ or —S(O)$_2$—R, where R is $C_1$–$C_6$ alkyl, amino, trifluoromethyl, $C_1$–$C_4$ alkylamino, di($C_1$–$C_4$)alkylamino, aryl, aryl($C_1$–$C_4$)alkyl, heterocycle, unsaturated heterocycle or $C_5$–$C_7$ cycloalkyl;

$R^1$ is aryl, $C_5$–$C_7$ cycloalkyl or —S—$R^{1x}$, where $R^{1x}$ is aryl or $C_5$–$C_7$ cycloalkyl;

$R^2$ is an amino acid side chain, —(CH$_2$)$_y$—X—$R^{2a}$, cyano ($C_1$–$C_4$)alkyl or —(CH$_2$)$_y$—S(O)$_w$—[1-N($R^{2c}$)-tetrazol-5-yl], where y is 0, 1, 2 or 3;

X is a bond, divalent ($C_2$–$C_4$)alkenyl, divalent ($C_2$–$C_4$)alkynyl, —C(O)—O, —O—C(O)—, —C(O)—NR$^{2b}$—, —NR$^{2b}$—C(O)—, —NR$^{2b}$—, —C(O)—, —O—, —S(O)$_w$—;

w is 0, 1 or 2;

$R^{2a}$ is $C_1$–$C_6$ alkyl, aryl, unsaturated heterocycle, heterocycle, aryl($C_1$–$C_4$)alkyl, unsaturated heterocycle ($C_1$–$C_4$)alkyl or heterocycle ($C_1$–$C_4$)alkyl;

$R^{2b}$ is hydrogen or $C_1$–$C_4$ alkyl;

$R^{2c}$ is hydrogen, $C_1$–$C_6$ alkyl, aryl, unsaturated heterocycle, aryl ($C_1$–$C_4$) alkyl or heterocycle ($C_1$–$C_4$) alkyl;

Y is aryl or unsaturated heterocycle;

$R^3$ is a group having the structure:

1) —C(O)—NR$^4$R$^4$,

2) 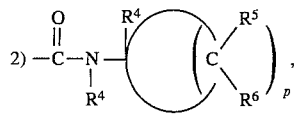

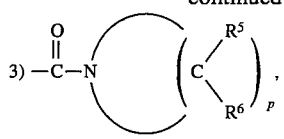

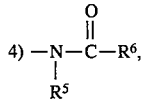

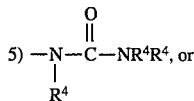

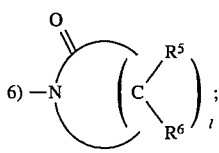

where:

p is 4 or 5;

l is 3, 4 or 5;

$R^4$ at each occurrence is independently hydrogen, $C_1$–$C_6$ alkyl or hydroxy ($C_1$–$C_4$) alkyl;

$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy ($C_1$–$C_4$) alkyl, carboxy, $C_1$–$C_4$ alkoxycarbonyl, carbamoyl, N—($C_1$–$C_4$) alkylcarbamoyl, aryl, heterocycle or unsaturated heterocycle;

with the proviso that when Z is hydrogen, formyl, carbamoyl, $C_2$–$C_6$ alkanoyl or $C_1$–$C_4$ alkoxycarbonyl; $R^2$ is an amino acid side chain or —$(CH_2)_y$—X—$R^{2a}$, where y is 0, 1, 2 or 3; X is a bond, —C(O)—O— or —C(O)—$NR^{2b}$—; $R^{2b}$ is hydrogen; and $R^{2a}$ is aryl, heterocycle or unsaturated heterocycle; then $R^1$ must be aryl or $C_5$–$C_7$ cycloalkyl; or a pharmaceutically acceptable salt thereof.

The present invention also relates to a compound of formula I, or a pharmaceutically acceptable salt thereof, wherein $R^1$, $R^2$, $R^3$, Y and Z are as defined above.

The present invention further provides pharmaceutical formulations comprising a compound of the present invention, or a pharmaceutically acceptable salt thereof, in combination with a pharmaceutically acceptable carrier, diluent or excipient therefor.

DETAILED DESCRIPTION OF THE INVENTION

The present invention provides new compounds of formula I, as described above, that are useful for treating or preventing HIV infection and/or AIDS.

All temperatures stated herein are in degrees Celsius (°C.). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl"

"Divalent($C_2$–$C_4$)alkenyl" represents a straight or branched divalent alkenyl chain having from two to four carbon atoms. Typical divalent($C_2$–$C_4$)alkenyl include ethenyl, 1-propenyl, 2-propenyl, 1-butenyl, 2-butenyl and the like.

"Divalent($C_2$–$C_4$)alkynyl" represents a straight or branched divalent alkenyl chain having from two to four carbon atoms. Typical divalent($C_2$–$C_4$)alkynyl include ethynyl, 1-propynyl, 2-propynyl, 1-butynyl, 2-butynyl and the like.

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo(Cl-$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Hydroxy($C_1$–$C_4$)alkyl" represents a straight or branched alkyl chain having from one to four carbon atoms with an hydroxy group attached to it. Typical hydroxy($C_1C_4$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl and the like.

"Cyano($C_1$–$C_4$)alkyl" represents a straight or branched alkyl chain having from one to four carbon atoms with a cyano group attached to it. Typical cyano($C_1$–$C_4$)alkyl groups include cyanomethyl, 2-cyanoethyl, 1-cyanoisopropyl, 2-cyanopropyl, 2-cyanobutyl, 3-cyanoisobutyl, cyano-t-butyl and the like.

"$C_1$–$C_4$ alkylthio" represents a straight or branched alkyl chain having from one to four carbon atoms attached to a sulfur atom. Typical $C_1$–$C_4$ alkylthio groups include methylthio, ethylthio, propylthio, isopropylthio, butylthio and the like.

"$C_1$–$C_4$ alkylthio($C_1$–$C_4$)alkyl" represents a straight or branched alkyl chain containing from one to four carbon atoms with a $C_1$–$C_4$ alkylthio group attached to it. Typical $C_1$–$C_4$ alkylthio($C_1$–$C_4$)alkyl groups include methylthioethyl, ethylthiobutyl, propylthioisopropyl, isopropylthiomethyl, butylthioethyl and the like.

"$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

"Di($C_1$–$C_4$)alkylamino" represents a straight or branched dialkylamino chain having two alkyl chains, each having independently from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"Carbamoyl($C_1$-$C_4$)alkyl" represents a straight or branched alkyl chain having from one to four carbon atoms with a carbamoyl group attached to it. Typical carbamoyl($C_1$-$C_4$)alkyl groups include carbamoylmethyl, carbamoylethyl, carbamoylpropyl, carbamoylisopropyl, carbamoylbutyl and carbamoyl-t-butyl and the like.

"N-{$C_1$-$C_4$)alkylcarbamoyl" represents a straight or branched alkyl chain having from one to four carbon atoms attached to the nitrogen atom of a carbamoyl moiety. Typical N-($C_1$-$C_4$)alkylcarbamoyl groups include N-methylcarbamoyl, N-ethytcarbamoyl, N-propylcarbamoyl, N-isopropylcarbamoyl, N-butylcarbamoyl, N-t-butylcarbamoyl and the like.

"$C_5$-$C_7$ cycloalkyl" represents a saturated hydrocarbon ring structure containing from five to seven carbon atoms which is unsubstituted or substituted with 1, 2 or 3 substituents independently selected from halo, halo($C_1$-$C_4$)alkyl, $C_1$-$C_4$ alkyl, $C_1$-$C_4$ alkoxy, carboxy, $C_1$-$C_4$ alkoxycarbonyl, carbamoyl, N-($C_1$-$C_4$)alkylcarbamoyl, amino, $C_1$-$C_4$ alkylamino, di($C_1$-$C_4$)alkylamino or a group having the structure —$(CH_2)_a$—$R^7$ where a is 1, 2, 3 or 4 and $R^7$ is hydroxy, $C_1$-$C_4$ alkoxy, carboxy, $C_1$-$C_4$ alkoxycarbonyl, amino, carbamoyl, $C_1$-$C_4$ alkylamino or di ($C_1$-$C_4$) alkylamino. Typical $C_5$-$C_7$ cycloalkyl groups include cyclopentyl, cyclohexyl, cycloheptyl, 3-methylcyclopentyl, 4-ethoxycyclohexyl, 5-carboxycycloheptyl, 6-chlorocyclohexyl and the like.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the abovedefined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1C_4$)alkyl, $C_1$-$C_4$ alkyl, $C_1$-$C_4$ alkoxy, carboxy, $C_1$-$C_4$ alkoxycarbonyl, carbamoyl, N-($C_1$-$C_4$)alkylcarbamoyl, amino, $C_1$-$C_4$ alkylamino, di($C_1$-$C_4$)alkylamino or a group having the structure —$(CH_2)_a$—$R^7$ where a is 1, 2, 3 or 4; and $R^7$ is hydroxy, $C_1$-$C_4$ alkoxy, carboxy, $C_1$-$C_4$ alkoxy-carbonyl, amino, carbamoyl, $C_1$-$C_4$ alkylamino or di($C_1$-$C_4$)-alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$-$C_4$)alkyl, $C_1$-$C_4$ alkyl, $C_1$-$C_4$ alkoxy, carboxy, $C_1$-$C_4$ alkoxycarbonyl, carbamoyl, N-($C_1$-$C_4$)alkylcarbamoyl, amino, $C_1$-$C_4$ alkylamino, di($C_1$-$C_4$)alkylamino or a group having the structure —$(CH_2)_a$—$R_7$ where a is 1, 2, 3 or 4; and $R^7$ is hydroxy, $C_1$-$C_4$ alkoxy, carboxy, $C_1$-$C_4$ alkoxy-carbonyl, amino, carbamoyl, $C_1$-$C_4$ alkylamino or di($C_1$-$C_4$)-alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydrisoquinolinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin- 7-yl, 4-methylpiperazinyl and the like.

"Unsaturated heterocycle($C_1$-$C_4$)alkyl" represents a straight or branched alkyl chain having from one to four carbon atoms with an unsaturated heterocycle group attached to it. Typical unsaturated heterocycle($C_1$-$C_4$)alkyl groups include pyrrolylmethyl, quinolinylmethyl, 1-indolylethyl, 2-furylethyl, 3-thien-2-ylpropyl, 1-imidazolylisopropyl, 4-thiazolylbutyl and the like.

"Aryl" represents a phenyl or naphthyl ring which is optionally substituted with 1, 2 or 3 substituents independently selected from halo, morpholino($C_1$-$C_4$)alkoxy, pyridyl ($C_1$-$C_4$)alkoxy, halo($C_1$-$C_4$)alkyl, $C_1$-$C_4$ alkyl, $C_1$-$C_4$ alkoxy, carboxy, $C_1$-$C_4$ alkoxycarbonyl, carbamoyl, N-($C_1$-$C_4$)alkylcarbamoyl, amino, $C_1$-$C_4$ alkylamino, di($C_1$-$C_4$)alkylamino or a group of the formula —$(CH_2)_a$—$R^7$ where a is 1, 2, 3 or 4; and $R^7$ is hydroxy, $C_1$-$C_4$ alkoxy, carboxy, $C_1$-$C_4$ alkoxycarbonyl, amino, carbamoyl, $C_1$-$C_4$ alkylamino or di($C_1$-$C_4$)alkylamino. Typical aryl groups include 4-methylphenyl, 3-ethylnaphthyl, 2,5-dimethylphenyl, 8-chloronaphthyl, 3-aminonaphthyl, 4-carboxyphenyl and the like.

"Aryl($C_1$-$C_4$)alkyl" represents a straight or branched alkyl chain having from one to four carbon atoms with an aryl group attached to it. Typical aryl($C_1$-$C_4$)alkyl groups include phenylmethyl, 2-phenylethyl, 3-naphthylpropyl, 1-naphthylisopropyl, 4-phenylbutyl and the like.

The term "amino acid side chains" represents the distinctive atom or group bonded to an α-carbon atom also having bonded thereto a carboxyl group and an amino group. These side chains are selected from those found on the following amino acids:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Thronine | Thr |

| | |
|---|---|
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl- 2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y. , 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, 8-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of the present invention may have three asymmetric centers as denoted by the asterisks in the formula below:

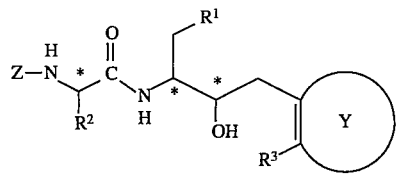

wherein $R^1$, $R^2$, $R^3$, Y and Z are as defined in formula I.

As a consequence of these asymmetric centers, the compounds of the present invention can occur as mixtures of diastereomers, racemic mixtures and as individual enantiomers. All asymmetric forms, individual isomers and combinations thereof, are within the scope of the present invention.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, maudelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

$R^1$ is phenyl;
Y is phenyl; and
$R^3$ is —C(O)NH(t-butyl);
or a pharmaceutically acceptable salt thereof.

Of these compounds, there are two groups of more preferred compounds. The first group consists of those compounds of formula IA

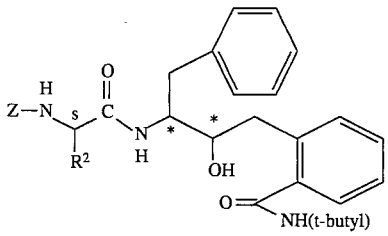

IA wherein:
Z is —S(O)$_2$—R, where
R is aryl, aryl($C_1$–$C_4$)alkyl or $C_5$–$C_7$ cycloalkyl; and
$R^2$ is —$CH_2CN$, —$CH(CH_3)$2 or —$CH_2$—C(O)$NH_2$; or a pharmaceutically acceptable salt thereof.

The second group consists of those compounds of formula IB wherein:

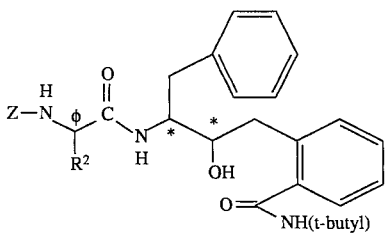

IB

Z is —C(O)CF$_3$, $C_2$–$C_6$ alkanoyl or —S(O)$_2$—R, where
R is $C_1$–$C_6$ alkyl;
$R^2$ is —(CH$_2$)$_y$—X—$R^{2a}$, where:
y is 1;
X is —C(O)—O—, —C(O)—NR$^{2b}$— or —S(O)$_w$—; and
$R^{2a}$ is aryl, heterocycle, aryl ($C_1$–$C_4$) alkyl heterocycle ($C_1$–$C_4$) alkyl or N($C_1$–$C_4$)alkyltetrazolyl; with the provisos that:
(1) when X is —C(O—O— or —C)O) —NR$^{2b}$—, then the asymmetric center denoted φ is an "R"; and
(2) when X is —S(O)$_w$—, then the asymmetric center denoted φ is an "S";
or a pharmaceutically acceptable salt thereof.

Even more preferred compounds of this second group are those compounds wherein:
Z is ethanoyl, —C(O) CF$_3$, or —S(O)$_2$—CH$_3$; and
$R^{2a}$ is phenyl, p-fluorophenyl, phenylmethyl, naphthyl, naphthylmethyl, pyridyl, quinolinyl, quinolinylmethyl or N-methyltetrazolyl; or a pharmaceutically acceptable salt thereof.

The most preferred compounds of the present invention are:

[2R-(2R*, 3S*, 6S*)]-N-t-butyl-2-[2-hydroxy-3-phenylmethyl- 4-aza-5-oxo-6-N(ethanoyl)amino-7-naphth-2-ylsulfonyl]heptyl benzamide;

[2R-(2R*, 3S*, 6S*)]-N-t-butyl-2-[2-hydroxy-3-phenylmethyl- 4-aza-5-oxo-6-N(methylsulfonyl)amino-7-naphth-2-ylthio]heptyl benzamide;

[2R-(2R*, 3S*, 6S*)]-N-t-butyl-2-[2-hydroxy-3-phenylmethyl- 4-aza-5-oxo-6-N(methylsulfonyl)amino-7-naphth-2-ylsulfonyl]heptyl benzamide;

[2R-(2R*, 3S*, 6S*)]-N-t-butyl-2-[2-hydroxy-3-phenylmethyl- 4-aza-5-oxo-6-N(methylsulfonyl)amino-7-phenylsulfinyl]heptyl benzamide;

[2R-(2R*, 3S*, 6S*)]-N-t-butyl-2-[2-hydroxy-3-phenylmethyl- 4-aza-5-oxo-6-N(methylsulfonyl)amino-7-quinolin- 2-ylsulfonyl]heptyl benzamide;

[2R-(2R*, 3S*, 6S*)]-N-8-butyl-2-[2-hydroxy-3-phenylmethyl- 4-aza-5-oxo-6-N(ethanoyl)amino-7-quinolin-2-ylsulfinyl]heptyl benzamide;

[2R-(2R*, 3S*, 6S*)]-N-t-butyl-2-[2-hydroxy-3-phenylmethyl- 4-aza-5-oxo-6-N (ethanoyl)amino-7-quinolin-2-ylsulfonyl]heptyl benzamide; and

[2R-(2R*, 3S*, 6S*)]-N-t-butyl-2-[2 -hydroxy-3-phenylmethyl- 4-aza-5-oxo-6-N(naphth-1-ylethylsulfonyl)amino-7-carbamoyl]heptyl benzamide;

[2R-(2R*,3S*, 6S*)]-N-t-butyl-2-[2-hydroxy-3-(methylsulfonyl)amino- 7-(p-phenylmethyl-4-aza-5-oxo-6-N-fluorophenylsulfinyl)]heptyl benzamide;

[2R-(2R*, 3S*, 6S*)]-N-C-butyl-2-[2-hydroxy-3-phenylmethyl- 4-aza-5-oxo-6-N(methylsulfonyl)amino-7-N(methyl) tetrazolylsulfinyl)]heptyl benzamide;

[2R-(2R*, 3S*, 6S*)]-N-8-Butyl-2-[2-hydroxy-3-phenylmethyl- 4-aza-5-oxo-6-N(trifluoromethylcarbonyl)amino-7-naphth-2-ylthio]heptyl benzamide;

or a pharmaceutically acceptable salt thereof.

The following list of compounds is provided to further illustrate compounds of formula I included within the scope of the invention:

[2R-(2R*, 3S*, 6S*)]-N-t-butyl-2-[2-hydroxy- 3-phenylthiomethyl-4-aza-5-oxo-6-N(propanoyl)amino-7-quinolin-2-ylsulfonyl]heptyl benzamide;

[2R-(2R*, 3S*, 6S*)]-N-t-butyl-2-[2-hydroxy-3-naphth-2-ylthiomethyl-4-aza-5-oxo-6-N(ethanoyl)amino-7-naphth- 2-ylsulfonyl]heptyl benzamide;

[2R-(2R*, 3S*, 6S*)]-N-t-butyl-2-[2-hydroxy-3-naphthylmethyl- 4-aza-5-oxo-6-N(ethanoyl)amino-8-naphth-2-ylsulfonyl]octyl benzamide

[2R-(2R*, 3S*, 6S*)]-N-8-butyl-2-[2-hydroxy-3-phenylthiomethyl- 4-aza-5-oxo-6-N(methylsulfonyl)amino-7-naphth- 2-ylthio]heptyl benzamide;

[2R-(2R*, 3S*, 6S*)]-N-8-butyl-2-[2-hydroxy-3-naphthylthiomethyl- 4-aza-5-oxo-6-N (methylsulfonyl) amino-7-quinolin- 2-ylthio]heptyl benzamide;

[2R-(2R*, 3S*, 6S*)]-N-t-butyl-2-[2-hydroxy-3-phenylthiomethyl- 4-aza-5-oxo-6-N (methylsulfonyl)amino-7-phenylsulfinyl]heptyl benzamide;

[2R-(2R*, 3S*, 6S*)]-N-t-butyl-2-[2-hydroxy-3-naphthylthiomethyl- 4-aza-5-oxo-6-N (methylsulfonyl)amino-8-phenylsulfinyl]octyl benzamide;

[2R-(2R*, 3S*, 6S*)]-N-t-butyl-2-[2-hydroxy-3-phenylmethyl- 4-aza-5-oxo-6-N(butylsulfonyl)amino-7-phenylsulfinyl]heptyl benzamide;

[2R-(2R*, 3S*, 6S*)]-N-t-butyl-2-[2-hydroxy-3-phenylmethyl- 4-aza-5-oxo-6-N (methylsulfonyl) amino-7 -benzthien- 2-ylsulfinyl]heptyl benzamide;

[2R-(2R*, 3S*, 6S*)]-N-t-butyl-2-[2-hydroxy-3-phenylthiomethyl- 4-aza-5-oxo-6-N (methylsulfonyl) amino-8-quinolin- 2-ylsulfonyl]octyl benzamide;

[2R-(2R*, 3S*, 6S*)]-N-t-butyl-2-[2-hydroxy-3-phenylmethyl- 4-aza-5-oxo-6-N(methylsulfonyl)amino-7-benzimidazolylsulfinyl]heptyl benzamide;

[2R-(2R*, 3S*, 6S*)]-N-t-butyl-2-[2-hydroxy-3phenylmethyl- 4-aza-5-oxo-6-N(propylsulfonyl)amino-7-pyrid-2-ylsulfinyl]heptyl benzamide;

[2R-(2R*, 3S*, 6S*)]-N-t-butyl-2-[2-hydroxy-3-phenylthiomethyl- 4-aza-5-oxo-6-N (ethylsulfonyl)amino-8-pyrid-3-ylsulfonyl]octyl benzamide;

[2R-(2R*, 3S*, 6S*)]-N-t-butyl-2-[2-hydroxy-3-phenylmethyl- 4-aza-5-oxo-6-N(naphth-1-ylpropylsulfonyl)amino- 7-carbamoyl]heptyl benzamide;

[2R-(2R*, 3S*, 6S*)]-N-t-butyl-2-[2-hydroxy-3-phenylthiomethyl- 4-aza-5-oxo-6-N(naphth-1-ylmethylsulfonyl)amino- 8- carbamoyl]octyl benzamide;

[2R-(2R*, 3S*, 6S*)]-N-t-butyl-2-[2-hydroxy-3-phenylmethyl- 4-aza-5-oxo-6-N (quinolin-2-ylmethyl sulfonyl)amino- 7-carbamoyl]heptyl benzamide;

[2R-(2R*, 3S*, 6S*)]-N-t-butyl-2-[2-hydroxy-3-phenylmethyl- 4-aza-5-oxo-6-N (pyrid-2-ylpropylsulfonyl)amino- 7-carbamoyl]heptyl benzamide;

or a pharmaceutically acceptable salt thereof.

The compounds of the present invention, or their precursors, can be prepared using procedures known in the art. More particularly, the compounds of formula I where $R^3$ is bonded through a carbonyl group (groups 1 through 3 in the definition of $R^3$) are prepared according to the procedures shown below in Reaction Scheme I.

Reaction Scheme I:

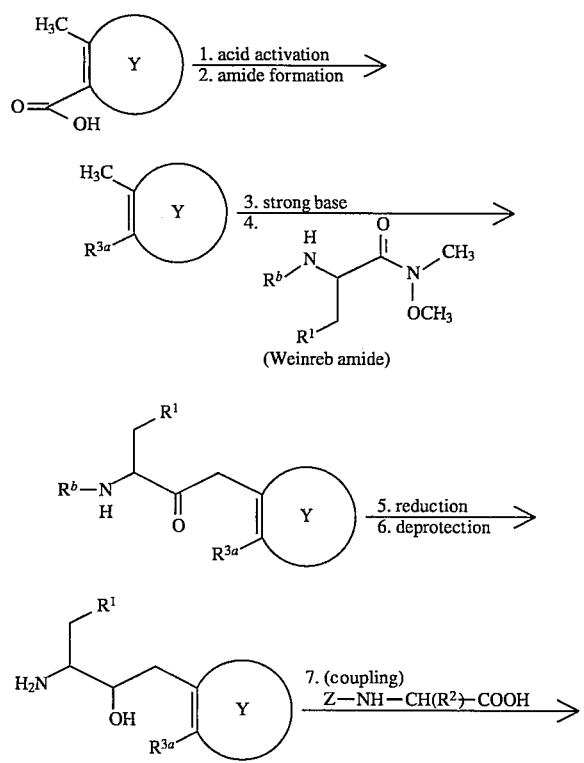

Reaction Scheme I:

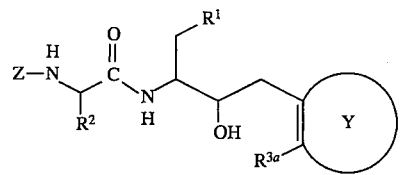

where:
$R^1$, $R^2$, $R^3$, Y and Z are as defined above for formula I;
$R^b$ is an amino-protecting group; and
$R^{3a}$ is group 1, 2 or 3 of $R^3$ as defined above.

Reaction Scheme I, above, is accomplished by carrying out the above chemical reactions in sequential order. Once a reaction is complete, the intermediate compound may be isolated, if desired, by procedures known in the art; for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction I.1, the reaction is typically carried out by activating, that is, converting, a suitably substituted aryl, heterocycle or unsaturated heterocycle carboxylic acid to the corresponding acyl chloride or acyl bromide by reaction with thionyl chloride, thionyl bromide, phosphorous trichloride, phosphorous tribromide, phosphorous pentabromide, phosphorous pentachloride or oxalylchloride according to procedures and under conditions known in the art. Suitable aryl, heterocycle or unsaturated heterocycle carboxylic acid compounds are commercially available or can be prepared by procedures known in the art.

In Reaction I.2, the acyl chloride or acyl bromide prepared in Reaction I.1 is reacted with ammonia or a primary or secondary amine having the formula:

$$H-NR^4R^4,$$

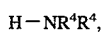

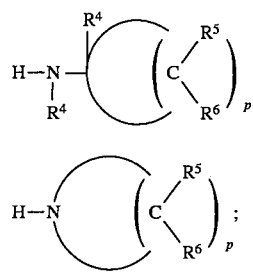

where $R^4$, $R^5$, $R^6$ and p are as defined above for formula I in a nonpolar aprotic solvent or mixture of solvents in the presence or absence of an acid scavenger to afford the corresponding amide. The reaction is carried out at a temperature of from about $-20°$ C. to about $25°$ C. Typical solvents for this reaction include ethers and chlorinated hydrocarbons, preferably diethylether, chloroform or methylene chloride. This reaction is preferably carried out in the presence of an acid scavenger such as a tertiary amine, preferably triethylamine.

In Reaction I.3, the amide prepared in Reaction I.2 is reacted with a strong base in the presence of a solubilizing agent to afford the corresponding action which is then reacted in Reaction I.4 with a Weinreb amide to afford a ketone. Reaction I.3 is carried out in an aprotic solvent at a temperature of from about −78° C. to about 0° C. Typical bases used in Reaction I.3 include lithium amide bases and alkyllithium bases, preferably $C_1$–$C_4$ alkyl lithium bases and lithium di($C_1$–$C_4$)alkylamide bases. Typical solubilizing agents for Reaction I.3 are tetramethyl($C_1$–$C_4$)-alkylenediamines, preferably tetramethylethylenediamine. Reaction I.4 is carried out in an aprotic solvent at a temperature from about −80° C. to about −40° C. Typical solvents for Reactions I.3 and I.4 include ethers, preferably tetrahydrofuran. In Reaction I.4, the anion is generally employed in an amount ranging from about equimolar proportions to about a three molar excess of the anion, preferably in about a two molar excess of the anion relative to the Weinreb amide reactant.

In Reaction I.5, the ketone prepared in Reaction I.3 is reduced to the corresponding alcohol using a suitable reducing agent. The reaction is carried out in a protic solvent at a temperature of from about −25° C. to about 25° C. Typical reducing agents for this reaction include sodium borohydride, lithium borohydride, diisobutylaluminum hydride, and sodium bis(2-methoxyethoxy)aluminum hydride. A preferred reducing agent is sodium borohydride. Typical protic solvents for this reaction include alcohols, preferably ethanol.

Reaction I.6 is a standard amino deprotection reaction using procedures and methods known in the art to afford the corresponding amine.

Reaction I.7 is a standard coupling reaction commonly employed in the synthesis of peptides which is carried out by reacting the amine prepared in Reaction 6, with a compound of the formula, Z—NH—CH($R^2$)—COOH, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran, dimethylformamide or methylene chloride. A preferred solvent is methylene chloride. The reaction is carried out at a temperature from about −30° C. to about 35° C., preferably from about 0° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexyl-carbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT.$H_2O$).

The compounds of formula I where $R^3$ is bonded through a nitrogen atom (groups 4 through 6 in the definition of $R^3$) can be prepared according to the procedures shown below in Reaction Scheme II.

Reaction Scheme II:

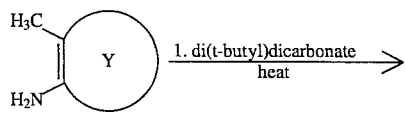

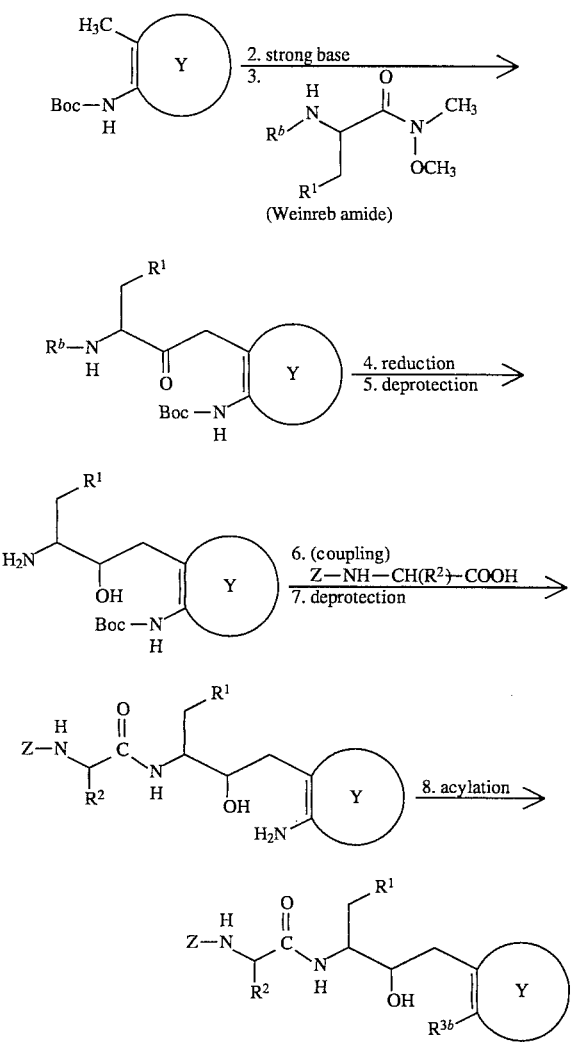

where:
$R^1$, $R^2$, Y and Z are as defined above for formula I;
$R^b$ is an amino-protecting group; and
$R^{3b}$ is group 4 through 6 of $R^3$ as defined above.

Reaction Scheme II, is accomplished by carrying out reactions 1–8 in sequential order. Once a reaction is complete, the intermediate compound may be isolated, if desired, by procedures known in the art; for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction II.1, a suitably substituted aryl, heterocycle or unsaturated heterocycle amine is protected, under standard conditions used with amino-protecting groups known in the art. Reactions 2 through 6 are carried out substantially as described above in Reaction Scheme I.3–I.7, with the exception that, in Reaction Scheme II, an additional deprotection reaction, Reaction II.7, is necessary to remove the amino-protecting group introduced in Reaction II.1. This is a standard amino deprotection reaction using procedures and methods known in the art. For example, the t-Boc group illustrated in Reaction Scheme II.1 may be removed using a strong acid, preferably trifluoroacetic acid.

In Reaction II.8, the illustrated intermediate is acylated with a suitable acyl halide, isocyanate or chloroformate, preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethylether, chloroform or methylene chloride.

Alternatively, compounds of formula I, where Z is $C_2$–$C_6$ alkanoyl, $C_1$–$C_4$ alkoxycarbonyl, carbamoyl or a group having the formula, —S(O)$_2$—R, where R is as defined above for formula I, can be prepared by first reacting the amine prepared in Reaction 1.6 or II.7 with a compound of the formula,

$R^b$—NH—CH($R^2$)—COOH wherein $R^2$ and $R^b$ are as defined above. The amino-protecting group is then removed from the resultant compound according to procedures and methods known in the art, to provide the corresponding amine. This amine may be acylated or sulfonylated according to procedures known in the art. For example, the amine compound may be acylated with a suitable acyl halide, isocyanate or chloroformate, preferably in the presence of an acid scavenger such as a tertiary amine, preferably triethylamine. The reaction is typically carried out at a temperature of from about −20° C. to about 25° C. Typical solvents for this reaction include ethers and chlorinated hydrocarbons, preferably diethylether, chloroform or methylene chloride. The amine may be sulfonylated by reaction with a suitably substituted sulfonylating agent in an aprotic solvent. Typical sulfonylating agents include appropriately substituted sulfonyl halides or sulfonic acid anhydrides. A preferred sulfonylating agent is the sulfonyl chloride of the formula R—SO$_2$–Cl. The reaction is typically carried out at a temperature from about —30° C. to about 50° C. in an aprotic solvent such as tetrahydrofuran. The amine reactant is generally employed in equimolar proportions relative to the carboxylic acid reactant, and preferably in the presence of equimolar quantities of an acid scavenger such as a tertiary amine. A preferred acid scavenger for this reaction is N-methylmorpholine (NMM).

In addition, compounds of formula I, wherein $R^2$ is —(CH$_2$)$_y$—X—$R^{2a}$, where y and $R^{2a}$ are as defined above in formula I and X is —C(O)—NR$^{2b}$—, can be prepared by first coupling the amine prepared in Reaction 1.6 or 11.7 with a compound of the formula,

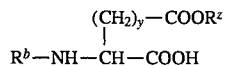

(CH$_2$)$_y$—COOR$^z$
|
R$^b$—NH—CH—COOH where:
R$^b$ is an amino-protecting group;
R$^z$ is a carboxy-protecting group; and
y is as defined above in formula I.

The carboxy-protecting group is then removed and the resultant compound is reacted with a suitably substituted amine reactant of the formula, $R^{2a}$—NH$_2$, according to the procedure detailed in Reaction I.7, above. A preferred solvent for this reaction is a mixture of tetrahydrofuran and dimethylformamide. A preferred coupling reagent for this reaction is DCC. A preferred promoting agent is HOBT.H$_2$O. The amino-protecting group is then removed from the resultant compound according to procedures and methods known in the art to provide the corresponding amine which may be acylated or sulfonylated according to the procedures discussed above.

The Weinreb amide used as a reactant in Reactions I.4 and II.3 is prepared by reacting an amino-protected amino acid with N-methoxy-N-methyl-amine in the presence of a promoting agent, an acid scavenger, and a coupling agent and preferably in the presence a promoting agent catalyst. The reaction is carried out in an aprotic solvent or mixture of solvents at a temperature of from about −25° C. to 25° C. A preferred promoting agent for this reaction is HOBT.H$_2$O. Preferred acid scavengers are the tertiary alkylamines, preferably triethylamine or N-methylmorpholine. A preferred coupling reagent is ethyldimethylaminopropylcarbodiimide hydrochloride. The Weinreb amide afforded by this reaction is preferably isolated prior to its use in Reaction Scheme I.4 and II.3.

The Weinreb amide where $R^1$ is a group having the structure —S—$R^{1x}$ can be prepared substantially in accordance with the reaction scheme described in Vederas et al., J.Am. Chem. Soc., 107, 7105–7109 (1985). In particular, this reaction scheme is carried out by reacting amino-protected serine with triphenylphosphine, dimethylazodicarboxylate (DMAD) or diethylazodicarboxylate (DEAD) in an aprotic solvent at a temperature of from about −80° C. to 0° C. to form the corresponding β-lactone compound. Typical solvents that can be used to accomplish this reaction include the ethers, such as tetrahydrofuran. The resulting lactone compound is then opened by reaction with an appropriately substituted thioanion having the structure, —S—$R^1$ to provide a carboxylic acid compound of the formula:

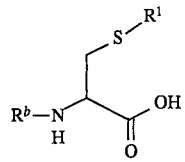

where $R^b$ and $R^1$ are as defined above. The thioanion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran. The resulting carboxylic acid compound is then reacted with N-methoxy-N-methyl-amine in the presence of a promoting agent, an acid scavenger, and a coupling agent in an aprotic solvent or mixture of solvents at a temperature of from about −25° C. to 25° C. A preferred promoting agent for this reaction is HOBT.H$_2$O. Preferred acid scavengers are tertiary alkylamines, preferably triethylamine or N-methylmorpholine. A preferred coupling reagent is ethyldimethylaminopropylcarbodiimide hydrochloride. The Weinreb amide afforded by this reaction is preferably isolated prior to its use in Reactions I.4 and II.3.

The carboxylic acid reactants used in the coupling reaction described in Reaction Scheme I.7 and II.6, to the extent not commercially available, are prepared using procedures known in the art. For example, the carboxylic acid reactants with "D" stereochemistry may be prepared substantially in accordance with the Vederas reaction scheme described above.

It will be understood by persons in the art that in performing the processes described above it may be desirable to introduce chemical protecting groups into the reactants in order to prevent secondary reactions from taking place. Any amine, alkylamine or carboxy groups which may be present on the reactants may be protected using any standard amino- or carboxy- protecting group which does not adversely affect the remainder of the molecule's ability to react in the manner desired. Preferred amino-protecting groups are t-Boc and Cbz. Preferred carboxy-protecting groups are benzhydryl, benzyl and allyl. The various protective groups may then be removed simultaneously or successively using methods known in the art.

As noted above, all asymmetric forms, individual isomers and combinations thereof are considered part of this invention. Such isomers may be prepared from their respective precursors by the procedures described above, by resolving the racemic mixtures, or by separating the diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting material in the synthesis of the compounds of this invention are known and, to the extent not commercially available are readily synthesized by standard procedures commonly employed in the art.

The pharmaceutically acceptable salts of the invention are typically formed by reacting a compound of formula I with an equimolar or excess amount of acid or base. The reactants are generally combined in a mutual solvent such as diethylether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS (FD)", "MS (FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

NMR spectra were obtained on a Brüker Corp. 270 MHz instrument or on a General Electric QE-300 300 MHz instrument. The chemical shifts are expressed in delta (δ) values (parts per million downfield from tetramethylsilane). MS(FD) spectra were taken on a Varian-MAT 731 Spectrometer using carbon dendrite emitters. EIMS were obtained on a CEC 21-110 instrument from Consolidated Electrodynamics Corporation. MS(FAB) spectra were obtained on a VG ZAB-3 Spectrometer. IR spectra were obtained on a Perkin-Elmer 281 instrument. UV spectra were obtained on a Cary 118 instrument. TLC was carried out on E. Merck silica gel plates. Melting points are uncorrected.

PREPARATION 1

A. N-t-Butyl-2-methylbenzamide

To a cold (0° C.) solution of 139.2 g (0.9 mol) of o-toluoyl chloride in 1200 mL of methylene chloride at 25° C., under nitrogen, was slowly added 180.0 g (1.8 mol) of triethylamine followed by the dropwise addition of a solution containing 73.14 g (1.0 mol) of t-butylamine in 200 mL of methylene chloride. The resulting reaction mixture was warmed to room temperature and allowed to react for 2.5 hours. The reaction mixture was then diluted with 1800 mL of water. The resulting organic and aqueous layers were separated, and the organic layer was washed sequentially with 2M sodium hydroxide, 1.0N hydrochloric acid and brine, dried over magnesium sulfate, filtered and then reduced to dryness under reduced pressure to provide 167.6 g of an off-white solid (mp 77°–78° C.).

Yield: 97%. $^1$H NMR (CDCl$_3$): δ 1.41 (s, 9H), 2.41 (s, 3H), 5.54 (br.s, 1H), 7.13–7.30 (m, 4H). IR (CHCl$_3$): 3430, 3011, 2971, 2932, 1661, 1510, 1484, 1452, 1393, 1366, 1304, 1216, 876 cm$^{-1}$. MS (FD): m/e 191(M+), 191(100). Analysis for C$_{12}$H$_{17}$NO: Calcd: C, 75.35; H, 8.76; N, 7.32; Found: C, 75.10; H, 9.11; N, 7.20.

B. (S)-N-t-Butyl-2-(3-(N-benzyloxycarbonyl)amino-2-oxo-4-phenylbutyl)benzamide

To a solution of 7.0 g (36 mmol) of the subtitled intermediate of Preparation 1A in 200 mL of anhydrous tetrahydrofuran, was added 12.1 mL (80.3 mmol) N,N,N',N'-tetramethylethylenediamine (TMEDA) was added via syringe. The resulting solution was cooled to −78° C. and then 55.9 mL of sec-butyllithium was added dropwise via syringe while maintaining the temperature of the reaction under −60° C. The resulting reaction solution was then allowed to stir for approximately 1 hour at −78° C. before the addition of a solution containing 5.00 g (14.6 mmol) of (S)-N-methoxy-N-methyl-2-(N-benzyloxycarbonyl) amino-3-phenylpropanamide in 50 mL anhydrous tetrahydrofuran was added via cannula while maintaining the reaction temperature below −65° C. The resulting reaction mixture was warmed to −20° C., quenched using 20 mL saturated ammonium chloride and then diluted with 200 mL of diethylether. The resulting layers were separated and the organic layer was washed sequentially with water, 0.2N sodium hydrogen sulfate and brine, dried over sodium sulfate and then reduced to dryness under reduced pressure to provide a colorless oil. This oil was purified using flash chromatography (eluent of 25% ethyl acetate in methylene chloride) to provide 6.08 g of a colorless foam. Yield: 88%. [a]$_D$ −289°–26° (c 0.12, MeOH). $^1$H NMR (CDCl$_3$) δ 1.38 (s, 9H), 2.99 (dd, J=15; 6 Hz, 1H), 3.24 (dd, J=15; 6 Hz, 1H, 3.89 (d, J=18 Hz, 1H), 4.16 (d, J=18 Hz, 1H), 4.72 (dd, J=15, 6 Hz, 1H), 5.00–5.09 (m, 2H) , 5.56 d, J=6 Hz, 1H), 5.93 (br. s, 1H) , 7.03–7.40 (m, 14H). IR (CHCl$_3$): 3431, 3027, 3012, 2973, 1713, 1658, 1511, 1454, 1383, 1366, 1307, 1231, 1046 cm$^{-1}$. MS (FD): m/e 472 (M$^+$), 218 (100). Analysis for C$_{29}$H$_{32}$N$_2$O$_4$: Calcd: C, 73.70; H, 6.82; N, 5.93; Found: C, 73.41; H, 6.98; N, 5.83.

C. [2R-(2R*,3S*)]-N-t-Butyl-2-(B-(N-benzyloxycarbonyl)amino- 2-hydroxy-4-phenylbutyl)benzamide To a solution of 6.96 g (14.7 mmol) of the subtitled intermediate of Preparation 1B in 200 mL absolute ethanol, under nitrogen, was added 2.78 g (73.5 mmol) sodium borohydride. When the reaction was substantially complete, as indicated by thin layer chromatography (TLC), the reaction mixture was diluted with 200 mL of ethyl acetate and quenched by the dropwise addition of 20 mL of saturated ammonium chloride. The resulting organic and aqueous layers were separated and the organic layer was washed sequentially with 1N hydrochloric acid, saturated sodium bicarbonate solution and brine, dried over sodium sulfate and then reduced to dryness under reduced pressure to provide 6.4 g of a colorless oil. This oil was purified using flash chromatography (gradient eluent of 2–10% methylene chloride in ethyl acetate) to provide 5.12 g of the desired subtitled intermediate.

Yield: 74%. $[\alpha]_D$ +10.38° (c 0.10, MeOH). $^1$H NMR (CDCl$_3$): δ 1.40 (s, 9H), 2.79 (dd, J=12; 3 Hz, 1H), 2.90–2.98 (m, 2H), 3.04 (44, J=12, 3 Hz, 1H), 3.70–3.81 (m, 1H), 3.97 (m, 1H), 4.96–5.08 (m, 2H), 5.10 (d, J=9 Hz, 1H), 5.88 (d, J=6 Hz, 1H), 5.93 (s, 1H), 7.13–7.42 (m, 14H). IR (CHCl$_3$): 3431, 3028, 3012, 2971, 1773, 1643, 1515, 1454, 1367, 1229, 1028 cm$^{-1}$. MS (FD): m/e 475 (M$^+$), 475 (100). Analysis for C$_{29}$H$_{34}$N$_2$O$_4$: Calcd: C, 73.39; H, 7.22; N, 5.99; Found: C, 73.12; H, 7.48; N, 5.62.

D. [2R-(2R*, 3S*)]-N-t-Butyl-2-(3-amino-2-hydroxy-4-phenylbutyl)benzamide

A suspension was prepared containing 41.0 g (120 mmol) of the subtitled intermediate of Preparation 1C and 500 mg of 10% palladium-on-carbon in 150 mL absolute ethanol. This suspension was shaken under 60 psi hydrogen in a Parr shaker apparatus. The 10% palladium-on-carbon catalyst was then removed by filtration. The resultant filtrate was reduced to dryness under reduced pressure to provide 31.1 g of a light yellow foam. This foam was used without further purification.

Yield: 96%. $[\alpha]_D$ +34.68° (c 1.0, MeOH). $^1$H NMR (CDCl$_3$): δ 1.46 (s, 9H), 2.71 (dd, J=13.7; 9.5 Hz, 1H), 2.84 (dd, J=13.3; 2.51 Hz, 1H), 2.95–3.06 (m, 2H), 3.23–3.29 (m, 1H), 3.84–3.90 (m, 1H), 6.23 (s, 1H),
7.19–7.37 (m, 12H). IR (CHCl$_3$): 3440, 3382, 3007, 2970, 2934, 1643, 1516, 1454, 1367, 1213 cm$^{-1}$. MS (FD): m/e 341 (M$^+$), 341 (100).

EXAMPLE 1

A. [2R-(2R*, 3S*, 6R*)]-N-t-Butyl-2-[2-hydroxy-3-phenylmethyl- 4-aza-5-oxo-6-N (t-butoxycarbonyl)amino-7-benzyloxycarbonyl]heptyl benzamide To a cold (0° C.) solution containing 1.0 g (2.9 mmol) of the subtitled intermediate of Preparation 1D, 0.44 g (3.2 mmol) of hydroxybenzotriazole hydrate (HOBT.H$_2$O) and 0.95 g (2.9 mmol) of (2R)-2-N(t-butoxycarbonyl)amino-4-oxo- 4-benzyloxybutanoic acid in 7 mL of a 6:1 tetrahydrofuran/dimethylformamide solution under nitrogen, was added 0.64 g (3.1 mmol) of dicyclohexylcarbodiimide (DCC). The resulting reaction mixture was allowed to react for approximately one hour at 0° C. and then overnight at room temperature. The reaction mixture was diluted with ethyl acetate and then filtered. The filtrate was then concentrated under reduced pressure, washed sequentially with a saturated sodium bicarbonate solution, water, a 5% citric acid solution and brine, dried over sodium sulfate, filtered and reduced to dryness under reduced pressure to provide a residue. This residue was then purified using flash chromatography (eluent of 2.5% methanol in methylene chloride) to provide 1.9 g of a white solid (m.p. 67°–72° C.).

Yield: 87%. Analysis for C$_{37}$H$_{47}$N$_3$O$_7$: Calcd: C, 68.82; H, 7.34; N, 6.51; Found: C, 69.16; H, 7.50; N, 6.56.

B. [2R-(2R*,3S*,6R*)]-N-t-Butyl-2-[2-hydroxy-3-phenylmethyl- 4-aza-5-oxo-6-amino-7-benzyloxycarbonyl]heptyl benzamide To a cold (0° C.) solution of 1.6 g (2.5 mmol) of the subtitled compound of Example 1A in 5 mL of methylene chloride under nitrogen, was added 4 mL of triethylsilane followed by 4 mL of trifluoroacetic acid. The resulting reaction mixture was allowed to react for approximately thirty minutes at 0° C. before being allowed to warm to room temperature. When the reaction was substantially complete, as indicated by TLC, the desired subtitled compound was concentrated under reduced pressure from methylene chloride to provide 2.4 g of crude material which was used without further purification.

C. [2R-(2R*, 3S*, 6R*)1-N-t-Butyl-2-[2-hydroxy-3-phenylmethyl- 4-aza-5-oxo-6-N(ethanoyl)amino-7-benzyloxycarbonyl]heptyl benzamide To a solution of 1.35 g (2.47 mmol) of the subtitled compound of Example 1B in 5 mL of methylene chloride, was added 0.26 mL (2.7 mmol) of acetic anhydride followed by 0.42 mL (5.2 mmol) of pyridine. The resulting reaction mixture was allowed to stir for approximately two hours. When the reaction was substantially complete, as indicated by TLC, the reaction mixture was washed with a cold (0° C.) solution of 10N hydrochloric acid. The resulting layers were separated and the organic layer was dried over sodium sulfate, filtered and then concentrated under reduced pressure to provide 1.5 g of a white solid. This solid was purified using flash chromatography (gradient eluent of 3–10% methanol in methylene chloride) to provide 0.6 g of a white solid.

Yield: 40%. MS (FAB): Calcd: 588.3073 Found: 588.3051.

The desired subtitled compound was also prepared substantially in accordance with the procedure detailed in Example 6, below, using 70 mg (0.090 mmol) of the subtitled compound of Example 1B, 21 μL (0.19 mmol) of NMM and 7.1 μL (1.0 mmol) of acetylchloride to provide 40 mg of a white solid. This solid was purified using flash chromatography (eluent of 4% methanol in methylene chloride) to provide 10 mg of the desired titled compound.

Yield: 19%. $^1$H NMR (CDCl$_3$): δ 1.45 (s, 9H), 1.90 (s, 3H), 2.33 (dd, J=6 Hz, 1H), 2.74–3.10 (m, 5H), 3.75 (m, 1H), 4.26 (m, 1H), 4.68 {m, 1H), 5.08 (s, 2H) , 6.10 (s, 1H), 6.70 (d, J=6 Hz, 1H), 6.90 (d, J=8 Hz, 1H), 7.10–7.40 (m, 14H). $^{13}$NMR (CDCl$_3$): 171.83,170.57, 169.89, 169.80, 138.23, 137.69,137.25, 135.32,130.96, 130.55, 129.44, 128.59, 128.41, 128.35, 128.26, 126.74, 126.48, 126.26, 74.98, 66.88, 55.52, 52.25, 49.03, 37.21, 36.38, 35.28, 33.77, 28.72, 24.89, 23.12. MS (FAB): Calcd: 588. 3073; Found: 588.3051 IR (CHCl$_3$): 2976, 1656, 1516 cm$^{-1}$. UV (EtOH): 203 nm (E=44,949). Analysis for C$_{33}$H$_{41}$N$_3$O$_7$S: Calcd: C, 63.54; H, 6.62; N, 6.74; Found: C, 63.73; H, 6.56; N, 6.52.

D. [2R-(2R*,3S*,6R*)]-N-t-Butyl-2-[2-hydroxy-3-phenylmethyl- 4-aza-5-oxo-6-N(ethanoyl)amino-7-carboxy] heptyl benzamide To a solution of the subtitled compound of Example 1C in 20 mL of methanol, was added 100 mg of 5% palladium-on-carbon catalyst and 0.5 g ammonium formate. When the reaction was substantially complete, as indicated by TLC, the reaction mixture was filtered through celite. The filtrate was concentrated under reduced pressure to provide a residue. This residue was diluted with 100 mL of a 1:1 water/ethyl acetate mixture. The resulting layers were separated and the organic layer was dried over sodium sulfate and then concentrated under reduced pressure to provide 100 mg of a white solid. The celite bed was washed with hot methanol and the resulting filtrate was concentrated under reduced pressure and diluted with an ethyl acetate/water mixture.

The resultant mixture was then washed with a saturated ammonium chloride solution and the resulting layers were separated and the organic layer was dried over sodium sulfate and then concentrated under reduced pressure to provide 130 mg of the desired subtitled compound. The aqueous layers obtained above were combined and acidified to pH 3 using 10N hydrochloric acid. The desired subtitled compound was then extracted using a solution of 15% isopropanol in chloroform. The extracts were then dried over sodium sulfate, filtered and concentrated under reduced pressure to provide 0.28 g of the desired subtitled compound as a white solid. Overall Yield: 0.51 g (55%).

EXAMPLE 2

[2R-(2R*, 3S*, 6R*)]-N-t-Butyl-2-[2-hydroxy-3 -phenylmethyl-4-aza- 5-oxo-6-N(ethanoyl)amino-8-oxo-9-aza-10-pyrid-2-yl]decyl benzamide To a cold (0° C.) solution containing 0.10 g (0.20 mmol) of the subtitled compound of Example 1D, 0.021 mL (0.20 mmol) of 2-(aminomethyl)pyridine and 0.030 g (0.22 mmol) of HOBT-H$_2$O in 2.5 mL of a 4:1 tetrahydrofurandimethylformamide solution, was added 0.043 g (0.21 mmol) of DCC. The resulting reaction mixture was allowed to react for approximately thirty minutes at 0° C. and then overnight at room temperature. When the reaction was substantially complete, as indicated by TLC, the reaction mixture was diluted with a 15% isopropanol in chloroform solution. The resulting mixture was washed sequentially with a dilute aqueous sodium bicarbonate solution, water, citric acid and then brine, the organic layer was dried over sodium sulfate, filtered and then concentrated under reduced pressure to provide 0.16 g of a solid. This solid was purified using flash chromatography (eluent of 10% methanol in methylene chloride) to provide 0.10 g of a white solid.

Yield: 83%. $^1$H NMR (CDCl$_3$): δ 1.44 (s, 9H), 1.90 (s, 3H), 2.25 (dd, J=6,9 Hz, 1H), 2.98–2.60 (m, 4H), 3.10 (dd, J=6,9 Hz, 1H), 3.72 (m, 1H), 4.20 (m, 1H), 4.44 (m, 2H), 4.65 (m, 1H), 5.95 (br.s, 1H), 6.20 (s, 1H), 7.38–7.10 (m, 12H), 7.43 (d, J=8 Hz, 1H), 7.62 (t, J=6 Hz, 1H), 8.41 (d, J=5 Hz, 1H). IR (CHCl$_3$): 3429, 3010, 1650, 1601, 1516, 1454 cm$^{-1}$. MS (FD): m/e 588 (M+). Analysis for C$_{33}$H$_{41}$N$_5$O$_5$: Calcd: C, 67.44; H, 7.03; N, 11.92; Found: C, 65.09; H, 6.82; N, 10.52.

EXAMPLE 3

[2R-(2R*, 3S*, 6R*)]-N-t-butyl-2-[2-hydroxy-3-phenylmethyl-4-aza- 5-oxo-6-N(ethanoyl)amine-8-oxo-8-N (quinolin-3-yl)amine]octyl benzamide The titled compound was prepared substantially in accordance with the procedure detailed in Example 2 using 0.13 g (0.26 mmol) of the subtitled compound of Example 1D, 38 mg (0.26 mmol) of 3-aminoquinoline, 39 mg (0.29 mmol) of HOBT-H$_2$O and 56 mg (0.27 mmol) of DCC to provide 0.24 g of a residue. This residue was purified using flash chromatography (eluent of 10% methanol in methylene chloride) to provide 30 mg of the desired titled compound.

Yield: 19%. $^1$H NMR (CDCl$_3$): δ 1.43 (s, 9H), 1.98 (s, 3H), 2.58 (m, 1H), 2.70–3.12 (m, 5H), 3.76 (m, 1H), 4.30 (m, 1H), 4.90 (m, 1H), 6.19 (s, 1H), 7.00–7.70 (m, 15H), 7.99 (d, J=8 Hz, 1H), 8.80 (s, 1H), 8.95 (s, 1H), 9.85 (br.s, 1H). MS (FD): m/e 623 (M$^+$). Analysis for C$_{36}$H$_{41}$N$_5$OS-0.5H$_2$O: Calcd: C, 68.33; H, 6.69; N, 11.07; Found: C, 68.12; H, 6.66; N, 10.89.

EXAMPLE 4

[2R-(2R*, 3S*, 6R *]-N-t-butyl-2-[2-hydroxy-3-phenylmethyl-4-aza- 5-oxo-6-N (ethanoyl) amino-8-oxo-9-aza-10-phenyl]decyl benzamide The titled compound was prepared substantially in accordance with the procedure detailed in Example 2 using 50 mg (0.10 mmol) of the subtitled compound of Example 1D, 11 μL (0.10 mmol) of benzylamine, 13.5 mg (0.100 mmol) of HOBT.H$_2$O and 21 mg (0.10 mmol) of DCC to provide 0.90 mg of a white solid. This solid was purified using flash chromatography (eluent of 8% methanol in methylene chloride) to provide 40 mg of the desired titled compound.

Yield: 68%. $^1$H NMR (CDCl$_3$): δ 1.45 (s, 9H), 1.90 (s, 3H), 2.20 (dd, J=6, 9 Hz, 1H), 2.55 (dd, J=4, 9 Hz, 1H), 2.75–3.00 (m, 3H), 3.10 (dd, J=4, 9 Hz, 1H , 3.73 (m, 1H), 4.20 (m, 1H), 4.30 (m, 2H), 4.60 (m, 1H), 6.14 (hr. s, 1H ), 6.50 (m, 1H), 7.08–7.39 (m, 14H), 7.43 (d, J=9 Hz, 1H). IR (CHCl$_3$): 3010, 1651, 1516, 1455 cm$^{-1}$. MS (FD): m/e 587 (H$^+$). Analysis for C$_{34}$H$_{42}$N$_4$O$_5$: Calcd: C, 69.60; H, 7.21; N, 9.55; Found: C, 69.78; H, 7.50; N, 9.83.

EXAMPLE 5

[2R-(2R*, 3S *, 6R*)]-N-t-butyl-2-[2-hydroxy-3-phenylmethyl-4-aza- 5-oxo-6-N (dimethylaminosulfonyl)amino-7-benzyloxycarbonyl]heptyl benzamide To a solution containing 0.11 g (0.20 mmol) of the subtitled compound of Example 1B and 56 μL (0.40 mmol) of triethylamine in 4 mL of methylene chloride, was added 22 μL (0.25 mmol) of dimethylsulfamoyl chloride, under nitrogen. When the reaction was substantially complete, as indicated by TLC, the reaction mixture was reduced to dryness under reduced pressure to provide a residue. This residue was purified using high performance liquid chromatography (eluent of 1:1 acetonitrile/water containing 1% ammonium acetate) to provide 50 mg of the desired titled compound.

Yield: 38%. $^1$H NHR (CDCl$_3$): δ 1.47 (s, 9H), 2.52 (dd, J=6,12 Hz, 1H), 2.67 (s, 6H), 2.75–3.00 (m, 4H), 3.09 (dd, J=5,9 Hz, 1H), 3.78 (m, 1H), 3.98 (m, 1H), 4.36 (m, 2H), 5.06 (s, 2H), 5.52 (d, J=9 Hz, 1H), 5.94 (hr. s, 1H), 6.98 (d, J=10 Hz, 1H), 7.10–7.41 (m, 14H) . IR (KBr): 3292, 1738, 1635, 1539, 1455 cm$^{-1}$. MS (FD): m/e 653 (M$^+$).

EXAMPLE 6

[2R-(2R*,3S*,6R*)]-N-t-butyl-2-[2-hydroxy-3-phenylmethyl-4-aza- 5-oxo-6-N(propanoyl)amino-7-benzyloxycarbonyl]heptyl benzamide To a solution containing 0.15 g (0.28 mmol) of the subtitled compound of Example 1B and 76 μL (0.55 mmol) of triethylamine in 4 mL of methylene chloride, was added 24 μL (0.28 mmol) of propionyl chloride, under nitrogen. When the reaction was substantially complete, as indicated by TLC, the reaction mixture was poured into 50 mL of a cold (0° C.) solution of 1N hydrochloric acid. The resulting layers were separated and the organic layer was dried over sodium sulfate, filtered and then reduced to dryness under reduced pressure to provide 0.17 g of a white solid.

Yield: quantitative. MS (FD): m/e 602(M$^+$). Analysis for C$_{35}$H$_{43}$N$_3$O$_6$: Calcd: C, 69.86; H, 7.20; N, 6.98; Found: C, 70.12; H, 7.27; N, 7.23.

EXAMPLE 7

[2R-(2R*, 3S *, 6R*)]-N-t-butyl-2-[2-hydroxy-3-phenylmethyl-4-aza- 5-oxo-6-N (butanoyl)amino-7-benzyloxycarbonyl]heptyl benzamide The titled compound was prepared substantially in accordance with the procedure detailed in Example 6 using 0.16 g (0.29 mmol) of the subtitled compound of Example 1B, 81 μL (0.58 mmol) of triethylamine and 30 μL (0.29 mmol) of butyryl chloride to provide 0.18 g of a white solid.

Yield: quantitative. MS (FD): m/e 616(M+). Analysis for $C_{36}H_{45}N_3O_6$: Calcd: C, 70.22; H, 7.37; N, 6.82; Found: C, 70.12; H, 7.37; N, 6.89.

EXAMPLE 8

A. [2R-(2R*,3S*, 6R*)]-N-t-butyl-2-[2-hydroxy-3-phenylmethyl- 4-aza-5-oxo-6-N(methylsulfonyl)amino-7-benzyloxycarbonyl]heptyl benzamide The subtitled compound was prepared substantially in accordance with the procedure detailed in Example 6 using 0.75 g (0.97 mmol) of the subtitled compound of Example 1B, 0.40 mL (2.91 mmol) of triethylamine and 75.1 µL (0.970 mmol) of methanesulfonylchloride to provide 0.60 g of a beige solid. This solid was purified using flash chromatography (eluent of 2% methanol in methylene chloride) to provide 0.33 g of a white solid.

Yield: 54%. $^1$H NMR (CDCl$_3$): δ 1.45 (s, 9 H), 2.42 (dd, J=6.12 Hz, 1H), 2.76 (s, 3H), 2.63–3.10 (m, 5H), 3.80 (m, 1H), 4.13 (m, 1H), 4.38 (m, 1H), 5.05 (s, 2H), 5.80 (d, J=8 Hz, 1H), 5.99 (d, J=6 Hz, 1H), 6.10 (s, 1H), 7.06–7.41 (m, 15H). MS (FD): m/e 623 (M+). IR (CHCl$_3$): 3026, 1660, 1643, 1602, 1517 cm$^{-1}$. UV (EtOH): 203 nm (E=44,949) . Analysis for $C_{33}H_{41}N_3O_7S$: Calcd: C, 63.54; H, 6.62; N, 6.74; Found: C, 63.73; H, 6.56; N, 6.52.

B. [2R-(2R*, 3S*, 6R*)]-N-t-butyl-2-[2-hydroxy-3-phenylmethyl- 4-aza-5-oxo-6-N(methylsulfonyl)amino-7-carboxy]heptyl benzamide The subtitled compound was prepared substantially in accordance with the procedure detailed in Example 1D using 0.13 g (0.21 mmol) of the subtitled compound of Example 8A, 0.2 g (3.2 mmol) of ammonium formate and 50 mg of palladium-on-carbon catalyst to provide 0.10 g of a white solid. This solid was used without further purification Yield: 91%.

EXAMPLE 9

[2R-(2R*, 3S*, 6R*)]-N-t-butyl-2-[2-hydroxy-3-phenylmethyl-4-aza- 5-oxo-6-N-(methylsulphonyl)amino-8-oxo-8-N (quinolin-2-yl)amino]octyl benzamide The titled compound was prepared substantially in accordance with the procedure detailed in Example 2 using 0.10 g (0.19 mmol) of the subtitled compound of Example 8B, 27 mg (0.19 mmol) of 2-aminoquinoline, 25 mg (0.19 mmol) of HOBT-H$_2$O and 39 mg (0.19 mmol of DCC to provide a crude material. This material was purified using flash chromatography (eluent of 3% methanol in methylene chloride) to provide 10 mg of the desired titled compound.

Yield: 8%. $^1$H NMR (CDCl$_3$): δ 1.43 (s, 9H), 2.60 (m, 2H), 2.85 (s, 3H), 2.80–3.12 (m, 4H), 3.79 (m, 1H), 4.28 (m, 1H), 4.40 (m, 1H), 5.90 (s, 1H), 6.03 (d, J=6 Hz, 1H), 6.22 (br. s, 1H), 7.10–7.30 (m, 11H), 7.42 (t, J=8 Hz, 1H), 7.61 (t, J=8 Hz, 1H), 7.75 (m, 2H), 8.02 (d, J=8 Hz, 1H), 8.81 (hr. s, 1H). MS (FD): m/e 660 (H+).

EXAMPLE 10

[2R-(2R*, 3S*, 6R*)]-N-t-butyl-2-[2-hydroxy-3-phenylmethyl-4-aza- 5-oxo-6-N(methylsulfonyl)amino-8-oxo-8-N(benzyl)amino]octyl benzamide The subtitled compound was prepared substantially in accordance with the procedure detailed in Example 2 using 0.11 g (0.21 mmol) of the subtitled compound of Example 8B, 22.5 µL (0.206 mmol) of benzylamine, 0.028 g (0.21 mmol) of HOBT-H$_2$O and 0.042 g (0.21 mmol) of DCC to provide a crude material. This material was purified using flash chromatography (eluent of 4% methanol in methylene chloride) to provide 70 mg of a white solid.

Yield: 54%. $^1$H NMR (CDCl$_3$): δ 1.45 (s, 9H), 2.33 (dd, J=6.12 Hz, 1H), 2.52 (dd, J=6.12 Hz, 1H), 2.75 (s, 3H), 2.71–3.10 (m, 4H), 3.75 (m, 1H), 4.15 (m, 1H), 4.24 (d, J=6 Hz, 2H), 4.28 (m, 1H), 5.92 (br. s, 1H), 6.06 (s, 1H), 6.26 (d, J=8 Hz, 1H), 6.47 (t, J=6 Hz, 1H), 7.10–7.41 (m, 15H). MS (FD): m/e 623 (M+). IR (CHCl$_3$): 3011, 1671, 1665, 1517, 1454 cm$^{-1}$. UV (EtOH): 204 nm (E=46,099). Analysis for $C_{33}H_{42}N_4O_6S$: Calcd: C, 63.64; H, 6.80; N, 9.00; Found: C, 63.86; H, 6.91; N, 8.77.

EXAMPLE 11

[2R-(2R*, 3S*, 6R*)]-N-t-butyl-2-[2-hydroxy-3-phenylmethyl-4-aza- 5-oxo-6-N(methylsulfonyl)amino-8-oxo-9-aza-10-quinolin- 2-yl]decyl benzamide The titled compound was prepared substantially in accordance with the procedure detailed in Example 2 using 0.25 g (0.47 mmol) of the subtitled compound of Example 8B, 200 mg (1.26 mmol) of 2-(aminomethyl)quinoline, 0.063 g (0.47 mmol) of HOBT-H$_2$O and 0.096 g (0.47 mmol) of DCC to provide a crude material. This material was purified using flash chromatography (gradient eluent of 2.5–10% methanol in methylene chloride) to provide 0.17 g of a white solid.

Yield: 53%. $^1$H NMR (CDCl$_3$): δ 1.42 (s, 9H), 2.50 (dd, J=6,12 Hz, 1H), 2.70–2.98 (m, 4H), 2.77 (s, 3H), 3.10 (dd, J=4,9 Hz, 1H), 3.78 (m, 1H), 4.30 (m, 2H), 4.58 (m, 2H), 5.93 (d, J=6 Hz, 1H), 6.18 (br. s, 1H), 6.40 (d, J=9 Hz, 1H), 7.10–7.32 (m, 9H), 7.48 (m, 3H), 7.67 (t, J=5 Hz, 1H), 7.73 (d, J=8 Hz, 1H), 8.00 (m, 2H). MS (FD): m/e 674 (M+). Analysis for $C_{36}H_{43}N_5O_6S$: Calcd: C, 64.17; H, 6.43; N, 10.39; Found: C, 64.01; H, 6.43; N, 10.14.

EXAMPLE 12

[2R-(2R*, 3S*, 6R*)]-N-t-butyl-2-[2-hydroxy-3-phenylmethyl-4-aza- 5-oxo-6-N(carbamoyl)amino-7-benzyloxycarbonyl]heptyl benzamide To a solution of 55 mg (0.10 mmol) of the subtitled intermediate of Example 1B in 2 mL of tetrahydrofuran, was added 19 µL (0.15 mmol) of trimethylsilylisocyanate. After allowing the reaction mixture to react for approximately thirty minutes at room temperature, an additional 35 µL (0.28 mmol) of trimethylsilylisocyanate were added and the resultant reaction mixture was allowed to react overnight. When the reaction was substantially complete, as indicated by TLC, the reaction mixture was concentrated under reduced pressure to provide a residue. This residue was redissolved in ethyl acetate and then washed sequentially with dilute aqueous sodium bicarbonate and brine solutions. The resulting layers were separated and the organic layer was dried over sodium sulfate, filtered and then reduced to dryness under reduced pressure to provide 40 mg of the desired titled compound.

Yield: 68%. $^1$ H NMR (CDCl$_3$): δ 1.43 (s, 9H), 2.43 (dd, J=6,12 Hz, 1H), 2.70–3.03 (m, 5H), 3.75 (m, 1H), 4.21 (m, 1H), 4.55 (m, 1H), 4.76 (s, 2H), 5.01 (s, 2H), 5.93 (br.s, 1H), 6.12 (d, J=8 Hz, 1H), 6.18 (s, 1H), 7.05 (d, J=8 Hz, 1H), 7.10–7.39 (m, 14H). MS (FD): 589 (M+) Analysis for $C_{33}H_{40}N_4O_6$: Calcd: C, 67.33; H, 6.85; N, 9.52; Found: C, 67.38; H, 6.89; N, 9.31.

EXAMPLE 13

A. [2R-(2R*,3S*,6R*)]-N-t-Butyl-2-[2-hydroxy-3-phenylmethyl- 4-aza-5-oxo-6-N(Carboxycarbonyl)amino-7-benzyloxy]heptyl benzamide The subtitled compound was prepared substantially in accordance with the procedure detailed in Example 1A using 0.42 g (1.23 mmol) of the subtitled compound of Preparation 1D, 0.36 g (1.23 mmol) of (R)-2-N (t-butoxycarbonyl)-3-benzyloxypropanoic acid, 0.17 g (1.23 mmol) of HOBT-H$_2$O and 0.25 g (1.23 mmol) of DCC to provide 0.64 g of a white solid. This solid was purified using flash chromatography (eluent of 2.5% methanol in methylene chloride) to provide 0.52 g of a white solid.

Yield: 68%.

B. [2R-(2R*,3S*,6R*)]-N-t-Butyl-2-[2-hydroxy-3-phenylmethyl- 4-aza-5-oxo-6-amino-7-benzyloxy]heptyl benzamide To a cold (0° C.) solution of 0.52 g (0.84 mmol) of the subtitled compound of Example 13A in 3 mL of methylene chloride, was added 3 mL of trifluoroacetic acid. The resulting reaction mixture was allowed to react for approximately twenty minutes at 0° C. and then one hour at room temperature. When the reaction was substantially complete, as indicated by TLC, the reaction mixture was concentrated under reduced pressure to provide a residue. This residue was dissolved in ethyl acetate, washed sequentially with a 5% ammonium hydroxide (aqueous) solution and brine, dried over sodium sulfate, filtered and then reduced to dryness under reduced pressure to provide 0.41 g of a crude material. This material was purified using flash chromatography (gradient eluent of 4–6% methanol in methylene chloride) to provide 0.28 g of a white solid.

Yield: 64%. MS (FD): m/e 518(M+). Analysis for C$_{31}$H$_{39}$N$_3$O$_4$: Calcd: C, 71.93; H, 7.59; N, 8.12; Found: C, 72.18; H, 7.46; N, 8.05.

C. [2R-(2R*, 3S*, 6R*)]-N-t-Butyl-2-[2-hydroxy-3-phenylmethyl- 4-aza-5-oxo-6-N(ethanoyl)amino-7-benzyloxy] heptyl benzamide The subtitled compound was prepared substantially in accordance with the procedure detailed in Example 6 using 95 mg (0.18 mmol) of the subtitled compound of Example 13B, 51 µL (0.37 mmol) of triethylamine and 13 µL (0.18 mmol) of acetyl chloride to provide 100 mg of the desired subtitled compound.

Yield: quantitative. $^1$H NMR (CDCl$_3$): δ 1.47 (s, 9H), 1.94 (s, 3H), 2.70–3.05 (m, 4H), 3.28 (m, 1H), 3.70 (m, 2H), 4.23–4.50 (m, 4H), 6.04 (br.s, 1H), 6.34 (d, J=7 Hz, 1H), 6.82 (d, J=9 Hz, 1H), 7.15–7.40 (m, 14H). MS (FD): m/e 560 (M$^+$). IR (KBr): 3283, 1640, 1549, 1453 cm$^{-1}$. UV (EtOH): 203 nm (44,370). Analysis for C$_{33}$H$_{41}$N$_3$O$_5$: Calcd: C, 70.81; H, 7.38; N, 7.51; Found: C, 71.09; H, 7.48; N, 7.25.

EXAMPLE 14

[2R-(2R*, 3S*, 6R*)]-N-t-Butyl-2-[2-hydroxy-3-phenylmethyl-4-aza- 5-oxo-6-N (methylsulfonyl)amino-7-benzyloxy]heptyl benzamide.

The titled compound was prepared substantially in accordance with the procedure detailed in Example 6 using 0.15 g (0.29 mmol) of the subtitled compound of Example 13B, 80 µL (0.58 mmol) of triethylamine and 22 µL (0.29 mmol) of methanesulfonylchloride to provide 0.15 g of crude material. This material was purified using flash chromatography (gradient eluent of 2–10% methanol in methylene chloride) to provide 80 mg of a white solid.

Yield: 47%. $^1$H NMR (CDCl$_3$): δ 1.45 (s, 9H), 2.78 (s, 3H), 2.77–3.07 (m, 4H), 3.40 (m, 1H), 3.64 (m, 1H), 3.78 (m, 1H), 3.94 (m, 1H), 4.35 (m, 1H), 4.40 (q, J=8 Hz, 2H), 5.35 (d, J=7 Hz, 1H), 5.98 (br. s, 1H), 7.10–7.40 (m, 15H). MS (FD ): m/e 596 (M$^+$). IR (KBr)= 3365, 1635, 1540, 1454 cm$^{-1}$. Analysis for C$_{32}$H$_{41}$N$_3$O$_6$S.0.5H$_2$O: Calcd: C, 63.55; H, 7.00; N, 6.95; Found: C, 63.74; H, 6.91; N, 6.94.

EXAMPLE 15

A. [2R-(2R*,3S*,6S*)]-N-t-Butyl-2-[2-hydroxy-3-phenylmethyl- 4-aza-5-oxo-6-N(t-butoxycarbonyl)amino-7-naphth- 2-ylthio]heptyl benzamide The subtitled compound was prepared substantially in accordance with the procedure detailed in Example 1A using 0.37 g (0.11 mmol) of the subtitled compound of Preparation 1D, 0.38 g (0.11 mmol) of (2S)-2-N(t-butoxycarbonyl)amino- 3-(naphth-2-ylthio)propanoic acid, 0.15 g (0.11 mmol) of HOBT-H$_2$O and 0.22 g (0.11 mmol) of DCC to provide 0.67 g of a white solid. This solid was isolated using flash chromatography (eluent of 2.5% methanol in methylene chloride) to provide 0.48 g of a white solid. This solid was used without further purification.

Yield: 66% (approx. 10% impurity). MS (FD): m/e 669(M$^+$). Analysis for C$_{39}$H$_{47}$N$_3$O$_5$S: Calcd: C, 69.93; H, 7.07; N, 6.27; Found: C, 70.21; H, 7.05; N, 6.36.

B. [2R-(2R*,3S*,6S*)]-N-t-Butyl-2-[2-hydroxy-3-phenylmethyl- 4-aza-5-oxo-6-amino-7-naphth-2-ylthio]heptyl benzamide The subtitled compound was prepared substantially in accordance with the procedure detailed in Example 13B using 0.48 g (0.72 mmol) of the subtitled compound of Example 15A and 3 mL of trifluoroacetic acid to provide 0.39 g of a white solid. This solid was purified using flash chromatography (eluent of 3.5% methanol in methylene chloride) to provide 0.29 g of a white solid.

Yield: 71%. MS (FD): 569 (M$^+$).

EXAMPLE 16

A. [2R-(2R*, 3S*, 6S*)]-N-t-Butyl-2-[2-hydroxy-3-phenylmethyl- 4-aza-5-oxo-6-N (ethanoyl)amino-7-naphth-2-ylthio]heptyl benzamide The subtitled compound was prepared substantially in accordance with the procedure detailed in Example 6 using 0.14 g (0.25 mmol) of the subtitled compound of Example 15B, 68 µL (0.49 mmol) of triethylamine and 18 µL (0.25 mmol) of acetyl chloride to provide 150 mg of a white solid.

Yield: quantitative. $^1$H NMR (CDCl$_3$): δ 1.43 (s, 9H), 1.80 (s, 3H), 2.70–3.20 (m, 6H), 3.77 (m, 1H), 4.32 (m, 1H), 4.55 (m, 1H), 6.08 (br. s, 1H), 6.45 (d, J=8 Hz, 1H), 6.90 (d, J=9 Hz, 1H), 7.11–7.45 (m, 12H), 7.70–7.80 (m, 4H). MS (FD): m/e 611 (M$^+$). IR (KBr): 3276, 1642, 1547, 1453 cm$^{-1}$. Analysis for C$_{36}$H$_{41}$N$_3$O$_4$S: Calcd: C, 70.68; H, 6.76; N, 6.87; Found: C, 70.73; H, 6.93; N, 6.84.

B. [2R-(2R*,3S*,6S*)]-N-t-Butyl-2-[2-hydroxy-3-phenylmethyl- 4-aza-5-oxo-6-N (ethanoyl)amino-7-naphth-2-ylsulfonyl]heptyl benzamide A solution of 0.10 g (0.49 mmol) of oxone® in 2 mL of water was slowly added to a cold (0° C.) solution of 0.10 g (0.16 mmol) of the subtitled compound of Example 16A in 3 mL of methanol, resulting in the formation of a white precipitate. The reaction mixture was allowed to react at room temperature for approximately two hours followed by dilution with a chloroform/water mixture. The resulting layers were separated and the organic layer was washed with brine, dried over sodium sulfate, filtered and then reduced to dryness under reduced pressure to provide 80 mg of a white solid. This solid was purified using flash chromatography (gradient eluent of 4–6% methanol in methylene chloride) to provide 50 mg of the desired subtitled compound.

Yield: 50%. $^1$H NMR (CDCl$_3$): δ 1.42 (s, 9H), 1.80 (s, 3H), 2.76–3.08 (m, 4H), 3.18 (m, 1H), 3.40 (m, 1H), 3.79 (m, 1H), 4.22 (m, 1H), 4.81 (m, 1H), 6.13 (br.s, 1H), 6.48 (d, J=8 Hz, 1H), 6.96–7.70 (m, 10H), 7.79 (d, J=7 Hz, 1H ), 7.91 (d, J=8 Hz, 1H), 8.00 (d, J=9 Hz, 2H), 8.45 (s, 1H). MS (FD): m/e 644 (M$^+$). Analysis for C$_{36}$H$_{41}$N$_3$O$_6$S 1.7H$_2$O:

Calcd: C, 64.11; H, 6.64; N, 6.23; Found: C, 64.04; H, 6.32; N, 6.15.

EXAMPLE 17

A. [2R-(2R*, 3S*, 6S*)]-N-t-Butyl-2-[2-hydroxy-3-phenylmethyl- 4-aza-5-oxo-6-N (methylsulfonyl)amine-7-naphth- 2-ylthio]heptyl benzamide The subtitled compound was prepared substantially in accordance with the procedure detailed in Example 6 using 0.14 g (0.25 mmol) of the subtitled compound of Example 15B, 68 µL (0.49 mmol) of triethylamine and 21 µL (0.27 mmol) of methanesulfonylchloride to provide 0.14 g of crude material. This material was purified using flash chromatography (gradient eluent of 2–5% methanol in methylene chloride) to provide 90 mg of the desired subtitled compound.

Yield: 56%. $^1$H NMR (CDCl$_3$): δ 1.43 (s, 9H), 2.72–3.10 (m, 6H), 2.75 (s, 3H), 3.80 (m, 1H), 3.91 (q, J=7 Hz, 1H), 4.39 (m, 1H), 5.63 (d, J=8 Hz, 1H), 5.96 (hr. s, 1H), 6.96 (d, J=9 Hz, 1H), 7.10–7.50 (m, 12H), 7.78 (m, 4H). MS (FD): m/e 647 (M$^+$). IR (KBr): 3272, 1635, 1522, 1454 cm$^{-1}$. Analysis for C$_{35}$H$_{41}$N$_3$O$_5$S$_2$: Calcd: C, 64.89; H, 6.38; N, 6.49; Found: C, 64.60; H, 6.36; N, 6.38.

B. [2R-(2R*,3S*,6S*)]-N-t-Butyl-2-[2-hydroxy-3-phenylmethyl- 4-aza-5-oxo-6-N (methylsulfonyl)amino-7-naphth- 2-ylsulfonyl]heptyl benzamide The subtitled compound was prepared substantially in accordance with the procedure detailed in Example 16B using 80 mg (0.12 mmol) of the subtitled compound of Example 17A and 78 mg (0.37 mmol) of oxone® to provide 80 mg of crude material. This material was purified using flash chromatography (gradient eluent of 2–3% methanol in methylene chloride) to provide 50 mg of the desired subtitled compound.

Yield: 60%. $^1$H NMR (CDCl$_3$): δ 1.46 (s, 9H), 2.70–3.33 (m, 6H), 2.92 (s, 3H , 3 .81 (m, 1H), 4.37 (m, 1H), 4.53 (m, 1H, 5 .73 (d, J=8 Hz, 1H), 6.04 (br. s, 1H), 6.92–7.40 (m, 10H), 7.68 (m, 2H), 7.83 (d, J=7 Hz, 1H), 7.93 (d, J=8 Hz, 1H), 8.00 (d, J=8 Hz, 12H), 8.50 (s, 1H). MS (FD): m/e 680(M$^+$). IR (CHCl$_3$): 3349, 1635, 1540, 1454 cm$^{-1}$. (EtOH): 203 nm (E=47,561); 230 nm (E=75,450). Analysis for C$_{35}$H$_{41}$N$_3$O$_7$S$_2$: Calcd: C, 61.83; H, 6.08; N, 6.18; Found: C, 62.05; H, 6.11; N, 6.14.

EXAMPLE 18

A. [2R-(2R*, 3S*, 6S*)]-N-t-Butyl-2-[2-hydroxy-3-phenylmethyl- 4-aza-5-oxo-6-N (ethanoyl)amino-7-benzylthio] heptyl benzamide The subtitled compound was prepared substantially in accordance with the procedure detailed in Example 1A using 0.27 g (0.79 mmol) of the subtitled compound of Preparation 1D, 0.20 g (0.79 mmol) of (2S)-2-N(ethanoyl)amino- 3-benzylthiopropanoic acid, 0.11 g (0.79 mmol) of HOBT.H$_2$O and 0.16 g (0.79 mmol) of DCC to provide 0.36 g of crude material. This material was purified using flash chromatography (gradient eluent of 2.5–5% methanol in methylene chloride) to provide 0.18 g of a white solid.

Yield: 40%. $^1$H NMR (CDCl$_3$): δ 1.45 (s, 9H), 1.87 (s, 3H), 2.38 (dd, J=6,12 Hz, 1H), 2.50 (dd, J=6,9 Hz, 1H), 2.70–3.10 (m, 4H), 3.61 (d, J=2 Hz, 2H), 3.77 (m, 1H) 4.28 (m, 1H), 4.45 (m, 1H), 5.90 (d, J=6 Hz, 1H), 6.25 (br.s, 1H), 6.48 (d, J=8 Hz, 1H ), 6.94 (d, J=9 Hz, 1H), 7.10–7.38 (m, 14H). MS (FD): m/e 575 (M$^+$). IR (CHCl$_3$): 3427, 3010, 1654, 1515, 1496, 1454 cm$^{-1}$. Analysis for C$_{33}$H$_{41}$N$_3$O$_4$S: Calcd: C, 68.84; H, 7.18; N, 7.30; Found: C, 69.12; H, 7.29; N, 7.38.

B. [2R-(2R*, 3S*, 6S*)]-N-t-Butyl-2-[2-hydroxy-3-phenylmethyl- 4-aza-5-oxo-6-N(ethanoyl)amino-7-benzylsulfonyl]heptyl benzamide The subtitled compound was prepared substantially in accordance with the procedure detailed in Example 16B using 49.0 mg (0.0850 mmol) of the subtitled compound of Example 18A and 53.6 mg (0.255 mmol) of oxone® to provide 50 mg of a white solid.

Yield: 96%. $^1$H NMR (CDCl$_3$): δ 1.46 (s, 9H), 1.99 (s, 3H), 2.70–3.13 (m, 5H), 3.34 (dd, J=4 Hz, 10H), 3.75 (m, 1H), 4.32 (m, 1H), 4.38 (q, J=10 Hz, 2H), 4.80 (m, 1H), 5.95 (s, 1H), 6.01 (d, J=6 Hz, 1H), 6.74 (d, J=7 Hz, 1H), 7.06 (d, J=10 Hz, 1H), 7.15–7.45 (m, 14H). MS (FD): m/e 608 (M$^+$). Analysis for C$_{35}$H$_{41}$N$_3$O$_7$S$_2$.1.5H$_2$O: Calcd: C, 62.44; H, 6.99; N, 6.62; Found: C, 62.34; H, 6.61; N, 6.53.

EXAMPLE 19

A. [2R-(2R*, 3S*, 6S*)]-N-t-Butyl-2-[2-hydroxy-3-phenylmethyl- 4-aza-5-oxo-6-N (t-butoxycarbonyl)amino-7-benzylthio]heptyl benzamide The subtitled compound was prepared substantially in accordance with the procedure detailed in Example 1A using 0.55 g (1.61 mmol) of the subtitled intermediate of Preparation 1D, 0.50 g (1.61 mmol) of (2S)- 2-N(t-butoxycarbonyl)amino-3-benzylthiopropanoic acid, 0.22 g (1.61 mmol) of HOBT.H$_2$O and 0.33 g (1.61 mmol) of DCC to provide 1.0 g of a white solid. This solid was purified using flash chromatography (eluent of 2% methanol in methylene chloride) to provide 0.74 g of a white solid. MS (FD): m/e 634(M$^+$).

Yield: 73%.

B. [2R-(2R*, 3S*, 6S*)]-N-t-Butyl-2-[2-hydroxy-3-phenylmethyl- 4-aza-5-oxo-6-amino-7-benzylthio]heptyl benzamide The subtitled compound was prepared substantially in accordance with the procedure detailed in Example 13B using 0.72 mg (1.14 mmol) of the subtitled compound of Example 19A and 3 mL of trifluoroacetic acid to provide 0.55 g of crude material. This material was purified using flash chromatography (gradient eluent of 4–6% methanol in methylene chloride) to provide 0.47 g of the desired subtitled compound.

Yield: 77%. MS (FD): m/e 534(M$^+$). Analysis for C$_{31}$HB$_{39}$N$_3$O$_3$S: Calcd: C, 69.76; H, 7.36; N, 7.87; Found: C, 70.03; H, 7.32; N, 7.63

C. [2R-(2R*,3S*,6S*)]-N-t-Butyl-2-[2-hydroxy-3-phenylmethylyl-4-aza-5-oxo-6-N (methylsulfonyl)amino-7-benzylthio]heptyl benzamide The subtitled compound was prepared substantially in accordance with the procedure detailed in Example 6 using 0.44 g (0.82 mmol) of the subtitled compound of Example 19B, 228 µL (1.65 mmol) of triethylamine and 77 µL (0.99 mmol) of methanesulfonyl-chloride to provide 0.50 g of a white solid. This solid was purified using flash chromatography (eluent of 2.5% methanol in methylene chloride) to provide 0.47 g of a white solid. Yield: 94%. $^1$H NMR (CDCl$_3$): δ1.50 (s, 9 H), 2.43 (dd, J=6.2,10 Hz, 1 H), 2.65 (dd, J=6.4,10 Hz, 1 H), 2.81 (s, 3 H), 2.80–3.10 (m, 4 H), 3.70 (s, 2 H) , 3.82 (m, 2 H), 4.40 (m, 1 H), 5.28 ( d, J=7.7 Hz, 1 H), 5.95 (s, 1 H), 6.78 (d, J=9.4 Hz, 1 H), 7.17–7.42 (m, 14 H) . MS (FD): m/e 611 (M$^+$). IR (KBr): 3274, 1635, 1537, 1454 cm$^{-1}$. Analysis for C$_{32}$H$_{41}$N$_3$O$_5$S$_2$: Calcd: C, 62;82; H, 6.75; N, 6.87; Found: C, 62.69; H, 6.67; N, 6.82.

D. [2R-(2R*,3S*,6S*)]-N-t-Butyl-2-[2-hydroxy-3-phenylmethyl-4-aza-5-oxo- 6-N(methylsulfonyl)amine-7-benzylsulfinyl]heptyl benzamide The subtitled compound was prepared substantially in accordance with the procedure detailed in Example 16B using 0.26 g (0.42 mmol) of the subtitled compound of Example 19C and 0.27 g (1.27 mmol) of oxone® to provide 0.21 g of a white solid. This solid was purified using flash chromatography (eluent of 2.5% methanol in methylene chloride) to provide 20 mg of a white solid. Yield: 7%. MS (FD): m/e 628 (M$^+$).

E. [2R-(2R*,3S*,6S*)]-N-t-Butyl-2- [2-hydroxy-3-phenyl-methyl-4-aza-5-oxo-6-N(methylsulfonyl)amino- 7-benzyl-sulfonyl]heptyl benzamide The subtitled compound was isolated from the reaction mixture detailed in Example 19D. Yield: 0.10 g (37%). $^1$H NMR (CDCl$_3$): δ1.46 (s, 9 H), 2.80 (m, 4 H), 2.90 (s, 3 H), 3.10 (m, 2 H), 3.80 (m, 1 H), 4.26 (q, J=4 Hz, 2 H), 4.38 (m, 2 H), 5.81 (d, J=9 Hz, 1 H), 6.00 (br.s, 1 H), 7.10–7.41 (m, 15 H). MS (FD): m/e 644(M$^+$). Analysis for C$_{32}$H$_{41}$N$_3$O$_7$S$_2$: Calcd: C, 59.70; H, 6.42; N, 6.53; Found: C, 59.95; H, 6.51; N, 6.45.

EXAMPLE 20

A. [2R(2R*,3S*,6S*)]-N-t-Butyl-2-[2-hydroxy-3-phenylm-ethyl- 4-aza-5-oxo-6-N(ethanoyl)amino- 7-phenylthio]hep-tyl benzamide The subtitled compound was prepared substantially in accordance with the procedure detailed in Example 1A using 0.28 g (0.84 mmol) of the subtitled intermediate of Preparation 1D, 0.20 g (0.84 mmol) of 2-N(ethanoyl)amino-3-phenylthiopropanoic acid (racemate), 0.11 g (0.84 mmol) of HOBT.H$_2$O and 0.17 g (0.84 mmol) of DCC to provide 0.43 g of a white solid. The resultant isomers were separated using flash chromatography (gradient eluent of 1.5–10% methanol in methylene chloride) to provide 0.13 g of a white solid. Yield: 28%. MS (FD): m/e 561(M$^+$). Analysis for C$_{32}$H$_{39}$N$_3$O$_4$S: Calcd: C, 68.42; H, 7.00; N, 7.48; Found: C, 68.38; H, 7.04; N, 7.46.

B. [2R-(2R*,3S*,6R*)]-N-t-Butyl- 2-[2-hydroxy-3-phenyl-methyl-4-aza-5-oxo- 6-N(ethanoyl)amino-7-phenylthio]heptyl benzamide The subtitled compound was isolated from the reaction mixture detailed in Example 20A. Yield: 0.13 g (28%). MS (FD): m/e 561 (M$^+$). Analysis for C$_{32}$H$_{39}$N$_3$O$_4$S: Calcd: C, 68.42; H, 7.00; N, 7.48; Found: C, 68.12; H, 7.00; N, 7.46.

C. [2R-(2R*,3S*,6S*)]-N-t-Butyl- 2-[2-hydroxy-3-phenyl-methyl-4-aza- 5-oxo-6-N(ethanoyl)amino-7-phenylsulfo-nyl]heptyl benzamide The subtitled compound was prepared substantially in accordance with the procedure detailed in Example 16B using 70 mg (0.12 mmol) of the subtitled compound of Example 20A and 79 mg (0.37 mmol) of oxone® to provide 70 mg of a white solid. Yield: 95%. $^1$H NMR (CDCl$_3$): δ1.43 (s, 9 H), 1.82 (s, 3 H), 2.75–3.12 (m, 5 H), 3.25 (m, 1 H), 3.80 (m, 1 H), 4.22 (m, 1 H), 4.82 (m, 1 H), 6.35 (br.s, 1 H), 6.62 (d, J=8 Hz, 1 H), 7.00–7.38 (m, 11 H) , 7.60 (m, 2 H), 7.85 (d, J=8 Hz, 2 H). MS (FD): m/e 594 (M$^+$). Analysis for C$_{32}$H$_{39}$N$_3$O$_6$S: Calcd: C, 64.73; H, 6.62; N, 7.08; Found: C, 64.59; H, 6.65; N, 6.78.

EXAMPLE 21

[2R-(2R*,3S*,6S*)]-N-t-Butyl- 2-[2-hydroxy-3-phenylm-ethyl-4-aza- 5-oxo-6-N(ethanoyl)amino-8-methylthio]octyl benzamide The titled compound was prepared substantially in accordance with the procedure detailed in Example 1A using 0.20 g (0.59 mmol) of the subtitled compound of Preparation 1D, 0.11 g (0.59 mmol) of (2S)- 2-N(ethanoyl)-amino-4-meth-ylthiobutanoic acid, 79 mg (0.59 mmol) of HOBT.H$_2$O and 0.12 g (0.59 mmol) of DCC to provide 0.30 g of a white solid. Yield: quantitative. MS (FD): m/e 514(M$^+$). Analysis for C$_{28}$H$_{39}$N$_3$O$_4$S: Calcd: C, 65.47; H, 7.65; N, 8.18; Found: C, 65.15; H, 7.55; N, 8.15.

EXAMPLE 22

A. [2R-(2R *,3S*,6S*)]-N-t-Butyl- 2-[2-hydroxy-3-phenyl-methyl-4-aza-5-oxo- 6-N(t-butoxycarbonyl)amino-7-phe-nylthio]heptyl benzamide The subtitled compound was prepared substantially in accordance with the procedure detailed in Example 1A using 2.0 g (5.74 mmol) of the subtitled compound of Preparation 1D, 1.9 g (5.74 mmol) of (2S)- 2-N(t-butoxycarbony-l)amino-3-phenylthiopropanoic acid, 0.8 g 5.74 mmol) of HOBT.H$_2$O and 1.2 g (5.74 mmol) of DCC to provide 3.4 g of a white solid. This solid was purified using flash chromatography (eluent of 2.5% methanol in methylene chloride) to provide 2.5 g of a white solid. Yield: 69%. Analysis for C$_{35}$H$_{45}$N$_3$O$_5$S: Calcd: C, 67.82; H, 7.32; N, 6.78; Found: C, 67.57; H, 7.20; N, 6.52.

B. [2R-(2R*,3S*,6S*)]-N-t-Butyl- 2-[2-hydroxy-3-phenyl-methyl- 4-aza-5-oxo-6-amino-7-phenylthio]heptyl benza-mide The subtitled compound was prepared substantially in accordance with the procedure detailed in Example 13B using 2.4 g (3.87 mmol) of the subtitled compound of Example 22A and 6 mL of trifluoroacetic acid to provide 2.1 g of a white foam. This foam was purified using flash chromatography (gradient eluent of 2.5–3.5% methanol in methylene chloride) to provide 1.1 g of the desired subtitled compound. Yield: 55%. Analysis for C$_{30}$H$_{37}$N$_3$O$_3$S: Calcd: C, 69.33; H, 7.18; N, 8.08; Found: C, 69.60; H, 7.43; N, 8.07.

C. [2R-(2R*,3S*,6S*)]-N-t-Butyl- 2-[2-hydroxy-3-phenyl-methyl- 4-aza-5-oxo-6-N(methylsulfonyl)amino- 7-phe-nylthio]heptyl benzamide The subtitled compound was prepared substantially in accordance with the procedure detailed in Example 6 using 1.0 g (1.9 mmol) of the subtitled compound of Example 22B, 0.53 mL (0.39 mmol) of triethylamine and 0.18 mL (0.23 mmol) of methanesulfonyl chloride to provide a crude material. This material was purified using flash chromatography (eluent of 2% methanol in methylene chloride) to provide 0.70 g of a white solid. Yield: 64%. MS (FD): m/e 597(M$^+$). Analysis for C$_{31}$H$_{39}$N$_3$O$_5$S$_2$.0.5H$_2$O: Calcd: C, 61.36; H, 6.64; N, 6.92; Found: C, 61.41; H, 6.51; N, 6.88.

D. [2R-(2R*,3S*,6S*)]-N-t-Butyl- 2-[2-hydroxy-3-phenyl-methyl- 4-aza-5-oxo-6-N(methylsulfonyl)amino- 7-phenyl-sulfonyl]heptyl benzamide The subtitled compound was prepared substantially in accordance with the procedure detailed in Example 16B using 0.51 g (0.85 mmol) of the subtitled compound of Example 22C and 0.63 g (2.99 mmol) of oxone® to provide 0.54 g of a white solid. This solid was purified using flash chromatography (eluent of 2% methanol in methylene chloride) to provide 0.47 g of a white solid. Yield: 87%. MS (FD): m/e 630(M$^+$). Analysis for C$_{31}$H$_{39}$N$_3$O$_7$S$_2$: Calcd: C, 59.12; H, 6.24; N, 6.67; Found: C, 58.89; H, 6.31; N, 6.81.

E. [2R-(2R*,3S*,6S*)]-N-t-Butyl- 2-[2-hydroxy-3-phenyl-methyl- 4-aza-5-oxo-6-N(methylsulfonyl)amino- 7-phenyl-sulfinyl]heptyl benzamide The subtitled compound was isolated from the reaction mixture detailed in Example 22D. $^1$H NMR (CDCl$_3$): δ1.42 (s, 9 H), 1.98 (t, J=13 Hz, 1 H), 2.52 (t, J=12 Hz, 1 H) , 2.83 (dd, J=3,13 Hz, 1 H) , 2.91 (s, 5 H), 3.25 (dd, J=4,14 Hz, 1

H), 3.67 {q, J=7 Hz, 1 H) , 4.30 (m, 1 H), 4.53 {t, J=9 Hz, 1 H) , 5.70 (d, J=10 Hz, 1 H) , 6.28 (br.s, 1 H) , 6.60 (m, 3 H), 7.02 (d, J=7 Hz, 2 H), 7.15–7.75 (m, 10 H) , 8.30 (d, J=10 Hz, 1 H). MS (FD): m/e 614 (M$^+$).

EXAMPLE 23

A. [2R-(2R*,3S*,6S*)]-N-t-Butyl- 2-[2-hydroxy-3-phenylmethyl- 4-aza-5-oxo-6-N(t-butoxycarbonyl)amino-7-quinolin-2-ylthio]heptyl benzamide The subtitled compound was prepared substantially in accordance with the procedure detailed in Example 1A using 1.8 g (5.2 mmol) of the subtitled compound of Preparation 1D, 1.8 g (5.2 mmol) of (2S)- 2-N(t-butoxycarbonyl)amino-4-(quinolin-2-ylthio)propanoic acid, 0.70 g (5.2 mmol) of HOBT.H$_2$O and 1.1 g (5.2 mmol) of DCC, in a 15 mL of tetrahydrofuran containing 2 mL of dimethylformamide, to provide 3.1 g of a yellow solid. This solid was purified using flash chromatography (eluent of 35% ethyl acetate in toluene) to provide 1.8 g of a white solid. Yield: 51%. $^1$H NMR (CDCl$_3$): δ1.40 (s, 9 H), 1.45 (s, 9 H), 2.95 (m, 4 H) , 3.57 (d, J=4 Hz, 2 H), 3.65 (m, 1 H), 4.30 (m, 1 H), 4.52 (q, J=5 Hz, 1 H), 6.02 (br.s, 2 H), 6.85 (d, J=9 Hz, 1 H), 7.10–7.38 (m, 10 H), 7.46 (t, J=7 Hz, 1 H), 7.70 (m, 2 H), 7.90 (d, J=9 Hz, 1 H), 8.04 (d, J=8 Hz, 1 H). MS (FD): m/e 670 (M$^+$). IR (KBr): 3292, 1715, 1637, 1594, 1518 cm$^{-1}$. UV (EtOH): 210 nm (E=58,247), 257 nm (E=23,586), 327 nm (E=5,628), 339 nm (E=6,082).

B. [2R-(2R*,3S*,6S*)]-N-t-Butyl- 2-[2-hydroxy-3-phenylmethyl- 4-aza-5-oxo-6-amino-7-quinolin-2-ylthio]heptyl benzamide The subtitled compound was prepared substantially in accordance with the procedure detailed in Example 13B using 2.4 g (3.87 mmol) of the subtitled compound of Example 23A and 6 mL of trifluoroacetic acid to provide 1.5 g of a white solid. A portion (0.5 g) of this solid was purified using flash chromatography (gradient eluent of 3–10% methanol in methylene chloride) to provide 0.43 g of the desired subtitled compound. The remaining 1.0 g of solid were used without further purification. Yield: 93%. Analysis for C$_{33}$H$_{38}$N$_4$O$_3$S: Calcd: C, 69.45; H, 6.71; N, 9.82; Found: C, 69.59; H, 6.58; N, 9.61.

C. [2R-(2R*,3S*,6S*)]-N-t-Butyl- 2-[2-hydroxy-3-phenylmethyl- 4-aza-5-oxo-6-N(methylsulfonyl)amino- 7-quinolin-2-ylthio]heptyl benzamide The subtitled compound was prepared substantially in accordance with the procedure detailed in Example 6 using 1.0 g (1.8 mmol) of the subtitled compound of Example 23B, 0.49 mL (3.6 mmol) of triethylamine and 0.16 mL (0.210 mmol) of methanesulfonyl chloride to provide 1.1 g of a light yellow solid. This solid was purified using flash chromatography (eluent of 40% ethyl acetate in toluene) to provide 0.54 g of a white solid. Yield: 49%. MS (FD): m/e 649(M$^+$). Analysis for C$_{34}$H$_{40}$N$_4$O$_5$S$_2$: Calcd: C, 62.94; H, 6.21; N, 8.64; Found: C, 62.67; H, 6.11; N, 8.42.

D. [2R-(2R*,3S*,6S*)]-N-t-Butyl- 2-[2-hydroxy-3-phenylmethyl- 4-aza-5-oxo-6-N(methylsulfonyl)amino- 7-quinolin-2-ylsulfonyl]heptyl benzamide To a cold (0° C.) solution of 0.17 g (0.262 mmol) of the subtitled compound of Example 23C in 5 mL of methylene chloride, was added 0.18 g (2 equiv.) of m-chloroperoxybenzoic acid (MCPBA) in two portions. The resultant reaction mixture was warmed to room temperature and then reacted for approximately ninety minutes. The reaction mixture was then diluted with methylene chloride and washed with a 1:9 sodium bicarbonate/brine mixture. The resulting layers were separated and the organic layer was dried over sodium sulfate and concentrated under reduced pressure to provide 0.21 g of a white solid. This solid was purified using flash chromatography (eluent of 40% toluene in ethyl acetate) to provide 110 mg of a white solid. Yield: 61%. $^1$H NMR (CDCl$_3$): 1.42 (s, 9 H), 2.80–3.00 (m, 3 H), 2.88 (s, 3 H) , 3.12 (dd, J=4.14 Hz, 1 H), 3.57 (dd, J=3.15 Hz, 1 H) , 3.80 (m, 2 H), 4.33 (m, 1 H), 4.51 (m, 1 H), 6.06 (br.s, 1 H) , 6.82 (d, J=7 Hz, 1 H), 7.05–7.40 {m, 9 H), 7.72 (t, J=8 Hz, 1 H), 7.90 (m, 2 H), 7.90 (m, 2 H), 8.10 (d, J=9 Hz, 1 H), 8.30 (d, J=9 Hz, 1 H), 8.44 (d, J=8 Hz, 1 H). MS (FD): m/e 681 (M$^+$). IR (KBr): 3284, 1675, 1634, 1531, 1454 cm$^{-1}$. UV (EtOH): 236 nm (E=48,422), 205 nm (E=58,708).

E. [2R-(2R*,3S*,6S*)]-N-t-Butyl- 2-[2-hydroxy-3-phenylmethyl- 4-aza-5-oxo-6-N(methylsulfonyl)amino- 7-quinolin-2-ylsulfinyl]heptyl benzamide The subtitled compound was isolated from the reaction mixture of Example 23D. Yield: 11%. Yield: 20 mg ( 11%). $^1$H NMR (CDCl$_3$): δ1.43 (s, 9 H), 2.70–3.21 (m, 6 H), 2.90 (s, 3 H), 4.38 (m, 1 H), 4.60 (m, 1 H), 5.66 (d, J=9 Hz, 1 H), 5.95 (br.s, 1 H) , 6.92–7.41 (m, 11 H), 7.80–8.00 (m, 4 H), 8.72 (d, J=9 Hz, 1 H).

EXAMPLE 24

A. [2R-(2R*,3S*,6S*)]-N-t-Butyl- 2-[2-hydroxy-3-phenylmethyl- 4-aza-5-oxo-6-N(ethanoyl)amino- 7-quinolin-2-ylthio]heptyl benzamide The subtitled compound was prepared substantially in accordance with the procedure detailed in Example 6 using 0.36 g (0.63 mmol) of the subtitled compound of Example 23B, 45 µL (0.63 mmol) of acetyl chloride and 175 µL (1.26 mmol) of triethylamine, to provide 0.36 g of a white solid. This solid was purified using flash chromatography (eluent of 3% methanol in methylene chloride) to provide 0.35 g of a white solid. Yield: 90%. MS (FD): m/e 612 (M$^+$).

B. [2R-(2R*,3S*,6S*)]-N-t-Butyl- 2-[2-hydroxy-3-phenylmethyl- 4-aza-5-oxo-6-N(ethanoyl)amino-7-quinolin- 2-ylsulfinyl]heptyl benzamide The subtitled compound was prepared substantially in accordance with the procedure detailed in Example 23D using 0.15 g (0.245 mmol) of the subtitled compound of Example 24B, 73 mg (0.95 equiv.) of MCPBA in 5 mL of methylene chloride, with the exception that the reactants were combined at −78° C., to provide 0.17 g of a white solid. This solid was purified using flash chromatography (gradient eluent of 3–6% methanol in methylene chloride) to provide 70 mg of a white solid. Yield: 47%. Analysis for C$_{35}$H$_{40}$N$_4$O$_5$S: Calcd: C, 66.86; H, 6.41; N, 8.91; Found: C, 67.13; H, 6.37; N, 8.63.

C. [2R-(2R*,3S*,6S*)]-N-t-Butyl- 2-[2-hydroxy-3-phenylmethyl- 4-aza-5-oxo-6-N(ethanoyl)amino- 7-quinolin-2-ylsulfonyl]heptyl benzamide.

The subtitled compound was prepared substantially in accordance with the procedure detailed in Example 23D using 110 mg (0.180 mmol) of the subtitled compound of Example 24B, 110 mg (1.95 equiv.) of MCPBA in 5 mL of methylene chloride, to provide 200 mg of a white solid. This solid was purified using flash chromatography (eluent of 4% methanol in methylene chloride) to provide 80 mg of a white solid. Yield: 67%. Analysis for C$_{35}$H$_{40}$N$_4$O$_6$S: Calcd: C, 65.20; H, 6.25; N, 8.69; Found: C, 65.49; H, 6.26; N, 8.61.

EXAMPLE 25

[2R-(2R*,3S*,6R*)]-N-t-Butyl- 2-[2-hydroxy-3-phenylmethyl- 4-aza-5-oxo-6-N-(ethanoyl)amino- 7-indol-3-yl]heptyl benzamide The titled compound was prepared substantially in accordance with the procedure detailed in Example 1A using 0.30 g (0.88 mmol) of the subtitled intermediate of Preparation 1D, 0.22 g (0.88 mmol) of 2-N(ethanoyl)amino- 3-indol-3-ylpropanoic acid (racemate), 0.12 g (0.88 mmol) of HOBT.$H_2O$ and 0.18 g (0.88 mmol) of DCC to provide 0.36 g of a white solid. This solid was purified using flash chromatography (eluent of 2% methanol in methylene chloride) to provide 40 mg of a white solid. Yield: 8%. $^1$NMR (CDCl$_3$): δ1.44 (s, 9 H), 1.82 (s, 3 H), 2.50 (dd, J=8,12 Hz, 1 H), 2.65–3.22 (m, 5 H), 3.39 (m, 1 H), 4.15 (m, 1 H), 4.60 (m, 1 H), 5.62 (br.s, 1 H) , 6.10 ( s, 2 H), 6.13 (s, 1 H), 6.90 (s, 1 H), 7.01–7.38 (m, 12 H), 7.62 (d, J=8 Hz, 1 H), 8.39 (br.s, 1 H). MS (FD): m/e 568(M$^+$). Analysis for $C_{34}H_{40}N_4O_4 \cdot 0.33CH_2Cl_2$: Calcd: C, 69.10; H, 6.87; N, 9.39; Found: C, 69.42; H, 6.61; N, 8.99.

EXAMPLE 26

[2R-(2R*,3S*,6R*)]-N-t-Butyl- 2-[2-hydroxy-3-phenylmethyl- 4-aza-5-oxo-6-N-(ethanoyl)amino-7-phenyl]heptyl benzamide The titled compound was prepared substantially in accordance with the procedure detailed in Example 1A using 0.13 g (0.38 mmol) of the subtitled intermediate of Preparation 1D, 79 mg (0.38 mmol) of (2R)-2-N(ethanoyl)-amino-3-phenylpropanoic acid, 52 mg (0.38 mmol) of HOBT.$H_2O$ and 79 mg (0.38 mmol) of DCC to provide 0.20 g of a white solid. Yield: quantitative. MS (FD): m/e 530(M$^+$).

EXAMPLE 27

A. [2R-(2R*,3S*,6R*)]-N-t-Butyl- 2-[2-hydroxy-3-phenylmethyl- 4-aza-5-oxo-6-N-(t-butoxycarbonyl)amino-7-naphth-2-ylcarbonyloxy]heptyl benzamide The subtitled compound was prepared substantially in accordance with the procedure detailed in Example 1A using 374 mg (1.1 mmol) of the subtitled intermediate of Preparation 1D, 410 mg (1.18 mmol) of (2R)-2-N(t-butoxycarbonyl)amino-3-(naphth-2-ylcarbonyloxy)propanoic acid, 149 mg (1.1 mmol) of HOBT.$H_2O$ and 227 mg (1.1 mmol) of DCC to provide 750 mg of a colorless foam. This foam was purified using flash chromatography (eluent of 35% ethyl acetate in toluene) to provide 570 mg of a white foam. Yield: 80%.

B. [2R-(2R*,3S*,6R*)]-N-t-Butyl- 2-[2-hydroxy-3-phenylmethyl- 4-aza-5-oxo-6-N-(ethanoyl)amino- 7-naphth-2-ylcarbonyloxy]heptyl benzamide To a cold (0° C.) solution of 100 mg (0.14 mmol) of the subtitled compound of Example 27A in 3 mL of methylene chloride, was added 1 mL of trifluoroacetic acid. The resulting reaction mixture was allowed to react for approximately thirty minutes at 0° C. and one hour at room temperature. The reaction mixture was then diluted with methylene chloride and concentrated under reduced pressure to provide a residue. This residue was redissolved in methylene chloride, and then washed sequentially with 20% aqueous ammonium hydroxide and brine. The resulting layers were separated and the organic layer was dried over sodium sulfate and then reduced to dryness under reduced pressure to provide 90 mg of a glassy material. This material was dissolved in methylene chloride and combined with 39 μL (0.28 mmol) of triethylamine and 11 μL (0.14 mmol) of acetyl chloride. After reacting for approximately ninety minutes at room temperature, the reaction mixture was diluted with ethyl acetate and washed sequentially with 1N aqueous hydrochloric acid, saturated sodium bicarbonate and brine solutions. The resulting layers were separated and the organic layer was dried over sodium sulfate, filtered and then reduced to dryness under reduced pressure to provide a colorless glass. This glass was purified using flash chromatography (eluent of 20% toluene in ethyl acetate) to provide 40 mg of the desired subtitled compound as a glassy material. Yield: 46%. Analysis for $C_{37}H_{41}N_3O_6$: Calcd: C, 71.25; H, 6.62; N, 6.74; Found: C, 71.32; H, 6.70; N, 6.67.

EXAMPLE 28

[2R-(2R*,3S*,6R*)]-N-t-Butyl- 2-[2-hydroxy-3-phenylmethyl- 4-aza-5-oxo-6-N-(methylsulfonyl) amino- 7-naphth-2-ylcarbonyloxy]heptyl benzamide The titled compound was prepared substantially in accordance with the procedure detailed in Example 27B, using 2 mL of trifluoroacetic acid, 350 mg (0.51 mmol) of the subtitled intermediate of Preparation 27A, 142 μL (1.02 mmol) of triethylamine and 48 μL (0.61 mmol) of methanesulfonyl chloride in 5 mL of methylene chloride to provide a residue. This residue was purified using flash chromatography (eluent of 50% ethyl acetate in toluene) to provide 240 mg of a white powder. Yield: 71%.

EXAMPLE 29

A. [2R-(2R*,3S*,6S*)]-N-t-Butyl- 2-[2-hydroxy-3-phenylmethyl- 4-aza-5-oxo-6-N (benzyloxycarbonyl)amino- 7-carbamoyl]heptyl benzamide The desired subtitled compound was prepared substantially in accordance with the procedure detailed in Example 1A, using 2.6 g (10 mmol) of (S)-2-N(benzyloxycarbonyl)amino-3-carbamoylpropanoic acid, 3.4 g ( 10 mmol) of the subtitled intermediate of Preparation 1D, 1.48 g (11 mmol) of HOBT.$H_2O$ and 2.4 g (11 mmol) of DCC in 4 mL of tetrahydrofuran, with the exception that 1.09 mL (10 mmol) of N-methylmorpholine was also added to the reaction mixture, to provide 4.4 g of the desired subtitled compound. Yield: 76%.

B. [2R-(2R*,3S*,6S*)]-N-t-Butyl- 2-[2-hydroxy-3-phenylmethyl- 4-aza-5-oxo-6-amino -7-carbamoyl]heptyl benzamide To a suspension of 0.5 g of 5% palladium-on-carbon in 95 mL of ethanol, was added 4 g (6.7 mmol) of the subtitled intermediate of Example 29A. The resulting reaction mixture was then stirred rapidly under 60 psi of hydrogen gas overnight at room temperature. When the reaction was complete, as determined by TLC, the 5% palladium-on-carbon was removed by filtration and the resulting solution was reduced to dryness under reduced pressure to provide 2.6 g of a solid. This solid was slurried in diethylether until substantially dissolved, and then concentrated under reduced pressure to provide a residue. This residue was recrystallized from an ethyl acetate/hexane mixture to provide 2.4 g of a solid. Yield: 80%. MS (FAB): m/e 455 (M$_{+1}$).

C. [2R-(2R*,3S*,6S*)]-N-t-Butyl- 2-[2-hydroxy-3-phenylmethyl- 4-aza-5-oxo-6-N(pyrid-2-ylsulfonyl)amino- 7-carbamoyl]heptyl benzamide The subtitled compound was prepared substantially in accordance with the procedure detailed in Example 6 using 75 mg (0.16 mmol) of the subtitled compound of Example 2BA, 40 μL (0.36 mmol) of N-methylmorpholine (NMM) and 35 mg {0.20 mmol) of pyrid-2-ylsulfonylchloride to provide a crude material. This material was purified using flash chromatography (eluent of 10% methanol in methylene chloride) to provide 70 mg of a white solid. Yield: 71%. $^1$H NMR (CDCl$_3$): δ1.45 (s, 9 H), 2.50 (dd, J=6,12 Hz, 1 H), 2.70–3.05 (m, 5 H), 3.66 (m, 1 H), 4.18 (m, 1 H), 4.40 (m, 1 H), 5.80 (br.s, 1 H), 6.04 (d, J=5 Hz, 1 H), 6.29 (br.s, 1 H), 6.40 (br.s, 1 H), 7.05 (d, J=8 Hz, 1 H), 7.10–7.40 (m, 10 H), 7.80–7.92 (m, 3H), 8.40 (d, J=5 Hz, 1 H). MS (FD): m/e 596($M^+$). IR (CHCl$_3$): 3408, 3025, 1678, 1660, 1517 cm$^{-1}$. Analysis for $C_{30}H_{37}N_5O_6S$: Calcd: C, 60.49; H, 6.26; N, 11.76; Found: C, 60.75; H, 6.42; N, 11.81.

EXAMPLE 30

[2R-(2R*,3S*,6S*)]-N-t-Butyl- 2-[2-hydroxy-3-phenylmethyl- 4-aza-5-oxo-6-N(quinolin-8-ylsulfonyl)amino- 7-carbamoyl]heptyl benzamide The titled compound was prepared substantially in accordance with the procedure detailed in Example 6 using 90 mg (0.20 mmol) of the subtitled compound of 29B, 22 μL (0.20 mmol) of NMM and 45 mg (0.20 mmol) of quinolin-8-ylsulfonylchloride to provide 50 mg of a crude material. This material was purified using flash chromatography (eluent of 10% methanol in methylene chloride) to provide 20 mg of a white solid. Yield: 15%. $^1$H NMR (CDCl$_3$): δ1.45 (s, 9 H), 1.82 (br.s, 1 H), 1.95 (m, 1 H), 2.57 (m, 1 H), 2.70–2.90 (m, 3 H), 3.05 (m, 1 H), 3.58 (m, 1 H), 4.09 (m, 2 H), 5.00 (br.s, 1 H), 5.60 (br.s, 1 H), 5.88 (br.s, 1 H), 6.10 (br.s, 1 H), 7.04–7.40 m, 9 H), 7.50–7.63 (m, 3 H), 8.05 (d, J=8 Hz, 1 H), 8.21 (d, J=8 Hz, 1 H), 8.33 (d, J=8 Hz, 1 H), 9.02 (m, 1 H). MS (FD): m/e 646 ($M^+$).

EXAMPLE 31

A. [2R-(2R*,3S*,6S*)]-N-t-Butyl- 2-[2-hydroxy-3-phenylmethyl- 4-aza-5-oxo-6-N(t-butoxycarbonyl)amino- 7-benzyloxycarbonyl] heptyl benzamide The subtitled compound was prepared substantially in accordance with the procedure detailed in Example 1A using 1.0 g (0.29 mmol) of the subtitled intermediate of Preparation 1D, 0.95 g (0.29 mmol) of (2S)-2-N(t-butoxycarbonyl)amino-3-benzyloxycarbonyl propanoic acid, 0.40 g (0.29 mmol) of HOBT.H$_2$O and 0.6 mg (0.29 mmol) of DCC to provide 1.90 g of a white solid. This solid was purified using flash chromatography (eluent of 2.5% methanol in methylene chloride) to provide 1.5 mg of a white foam. Yield: 79%. Analysis for $C_{37}H_{47}N_3O_7$: Calcd: C, 68.82; H, 7.34; N, 6.54; Found: C, 68.65; H, 7.20; N, 6.77.

B. [2R-(2R*,3S*,6S*)]-N-t-Butyl- 2-[2-hydroxy-3-phenylmethyl- 4-aza-5-oxo-6-amino-7-benzyloxycarbonyl]heptyl benzamide To a cold (0° C.) solution of the subtitled compound of Example 31A in 5 mL of methylene chloride, was added 1 mL of triethylsilane, followed by 2 mL of trifluoroacetic acid. After reacting for approximately thirty minutes the reaction mixture was warmed to room temperature and allowed to react an additional sixty minutes. When the reaction was substantially complete, as indicated by TLC, the reaction mixture was concentrated under reduced pressure to provide 2.1 g of a colorless oil. This oil was purified using flash chromatography (gradient eluent of 3–10% methanol in methylene chloride) to provide 0.75 g of a white solid. Yield: 42%.

C. [2R-(2R*,3S*,6S*)]-N-t-Butyl- 2-[2-hydroxy-3-phenylmethyl- 4-aza-5-oxo-6-N(methylsulfonyl)amino- 7-benzyloxycarbonyl]heptyl benzamide The subtitled compound was prepared substantially in accordance with the procedure detailed in Example 6 using 0.20 g (0.26 mmol) of the subtitled compound of Example 31B, 88 μL (0.80 mmol) of NMM and 22 μL (0.28 mmol) of methanesulfonyl chloride to provide 0.20 g of a crude material. This material was purified using flash chromatography (eluent of 2% methanol in methylene chloride) to provide 70 mg of a white solid. Yield: 44%. Analysis for $C_{33}H_{41}N_3O_7S$: Calcd: C, 63.54; H, 6.62; N, 6.74; Found: C, 63.80; H, 6.68; N, 6.73.

EXAMPLE 32

[2R-(2R*,3S*,6R*)]-N-t-Butyl- 2-[2-hydroxy-3-phenylmethyl- 4-aza-5-oxo-6-N-(ethanoyl)amino-7-benzylthio] heptyl benzamide The titled compound was prepared substantially in accordance with the procedure detailed in Example 1A using 0.43 g (1.3 mmol) of the subtitled intermediate of Preparation 1D, 0.32 g (1.3 mmol) of (R)-2-N(ethanoyl)amino-3-benzylthiopropanoic acid, 0.17 g (1.3 mmol) of HOBT.H$_2$O and 0.26 g (1.3 mmol) of DCC to provide 0.65 g of a white solid. This solid was purified using flash chromatography (eluent of 2.5% methanol in methylene chloride) to provide 70 mg of a white solid. Yield: 44%. MS (FD): m/e 575 ($M^+$). Analysis for $C_{33}H_{41}N_3O_4S$: Calcd: C, 68.84; H, 7.18; N, 7.30; Found: C, 69.09; H, 7.45; N, 7.42.

EXAMPLE 33

[2R-(2R*,3S*,6S*)]-N-t-Butyl- 2-[2-hydroxy-3-phenylmethyl- 4-aza-5-oxo-6-N (naphth-1-ylsulfonyl) amino- 7-carbamoyl]heptyl benzamide To a solution containing 200 mg (0.440 mmol) of the subtitled compound of Example 29B and 0.053 mL (0.485 mmol) of NMM in 8 mL of anhydrous tetrahydrofuran, was added 105 mg (0.462 mmol) of naphth-1-ylsulfonyl-chloride. The resulting reaction mixture was allowed to stir overnight at room temperature. When the reaction was substantially complete as indicated by TLC (using a solvent system of 10% methanol in chloroform), the reaction mixture was reduced to dryness under reduced pressure to provide a residue. This residue was diluted with ethyl acetate and then washed sequentially with saturated potassiumhydrogensulfate, brine and sodium bicarbonate. The resultant solution was dried over magnesium sulfate, filtered and reduced to dryness under reduced pressure to provide 300 mg of a white foam. This foam was purified using flash chromatography (silicon dioxide; eluted with 5% methanol in chloroform) to provide 190 mg of a white foam. Yield: 67%. MS (FD): m/e 645 ($M^{+1}$). Analysis for $C_{35}H_{40}N_4O_6S$: Calcd: C, 65.20; H, 6.25; N, 8.69; Found: C, 65.49; H, 6.29; N, 8.48.

EXAMPLE 34

[2R-(2R*,3S*,6S*)]-N-t-Butyl- 2-[2-hydroxy-3-phenylmethyl- 4-aza-5-oxo-6-N (naphth-2-ylsulfonyl)amino- 7-carbamoyl]heptyl benzamide The titled compound was prepared substantially in accordance with the procedure detailed in Example 33 using 200 mg (0.440 mmol) of the subtitled intermediate of Example 29B, 0.053 mL (0.485 mmol) of NMM and 105 mg 0.462 mmol) of naphth-2-ylsulfonylchloride. The resultant material was purified using flash chromatography (silicon dioxide; 3% methanol in chloroform) to provide 217 mg of the desired titled product as a white foam. Yield: 77%. MS (FD): m/e 645 ($M^{+1}$). Analysis for $C_{35}H_{40}N_4O_6S$: Calcd: C, 65.20; H, 6.25; N, 8.69; Found: C, 65.50; H, 6.42; N, 8.82.

EXAMPLE 35

[2R-(2R*,3S*,6S*)]-N-t-Butyl- 2-[2-hydroxy-3-phenylmethyl- 4-aza-5-oxo-6-N (naphth-1-ylethylsulfonyl)amino-7-carbamoyl]heptyl benzamide A solution of 118 mg (0.462 mmol) of naphth-1-ylethylsulfonylchloride in 8 mL of tetrahydrofuran was slowly added to a cold (0° C.) solution of 200 mg (0.440 mmol) of the subtitled compound of Example 29B and 0.053 mL (0.485 mmol) of NMH in 8 mL of tetrahydrofuran. The resulting reaction mixture was allowed to stir overnight. When the reaction was substantially complete as indicated by TLC, the reaction mixture was reduced to dryness under reduced pressure to provide a residue. This residue was diluted with ethyl acetate, and then washed sequentially with saturated potassiumhydrogensulfate, brine and sodium bicarbonate. The resultant solution was dried over magnesium sulfate, filtered and reduced to dryness under reduced pressure to provide a residue. This residue was purified using flash chromatography (silicon dioxide; eluted with 3% methanol in chloroform) to provide 126 mg of a white foam. Yield: 42.5%. MS (FD): m/e 673 ($M^{+1}$). Analysis for $C_{37}H_{44}N_4O_6S$: Calcd: C, 66.05; H, 6.59; N, 8.33; Found: C, 66.30; H, 6.72; N, 8.22.

EXAMPLE 36

[2R-(2R*,3S*,6S*)]-N-t-Butyl- 2-[2-hydroxy-3-phenylmethyl- 4-aza-5-oxo-6-N(naphth-2-ylmethylsulfonyl)amino-7-carbamoyl]heptyl benzamide The titled compound was prepared substantially in accordance with the procedure detailed in Example 33 using 1.36 g (6 mmol) of the subtitled intermediate of Example 2BA, 0.033 mL of NMM and 1.26 g (6 mmol) of naphth-2-ylmethylsulfonylchloride in 50 mL of methylene chloride, under nitrogen to provide 400 mg of a white foam. Yield: 77%. Analysis for $C_{37}H_{42}N_3O_6S$: Calcd: C, 65.63; H, 6.43; N, 8.50; Found: C, 65.52; H, 6.45; N, 8.43.

EXAMPLE 37

A. [2R-(2R*,3S*,6S*)]-N-t-Butyl- 2-[2-hydroxy-3-phenylmethyl- 4-aza-5-oxo-6-N(t-butoxycarbonyl)amino- 7-(p-fluorophenylthio)]heptyl benzamide The subtitled compound was prepared substantially in accordance with the procedure detailed in Example 1A using 1.2 g (3.49 mmol) of the subtitled compound of Preparation 1D, 1.1 g (3.49 mmol) of (2S)-2-N(t-butoxycarbonyl)amino-3-p-fluorophenylthiopropanoic acid, 0.47 g (3.49 mmol) of HOBT.H$_2$O and 0.72 g (3.49 mmol) of DCC to provide 2.1 g of a white solid. This solid was purified using flash chromatography (eluent of 3% methanol in methylene chloride) to provide 1.7 g of a white solid. Yield: 77%. MS (FD): 637($M^+$). Analysis for $C_{35}H_{44}FN_3O_5S$: Calcd: C, 65.91; H, 6.95; N, 6.59; Found: C, 65.71; H, 6.92; N, 6.50.

B. [2R-(2R*,3S*,6S*)]-N-t-Butyl- 2-[2-hydroxy-3-phenylmethyl- 4-aza-5-oxo-6-amino-7-(p-fluorophenylthio)]heptyl benzamide The subtitled compound was prepared substantially in accordance with the procedure detailed in Example 13B using 1.7 g (2.67 mmol) of the subtitled compound of Example 37A and 5 mL of trifluoroacetic acid to provide 1.4 g of a white solid. This solid was purified using flash chromatography (gradient eluent of 2.5–3% methanol in methylene chloride) to provide 0.83 g of a white solid (m.p. 63°–65° C.). Yield: 59%. MS (FD): 538($M^+$). Analysis for $C_{30}H_{36}FN_3O_3S$: Calcd: C, 67.01; H, 6.75; N, 7.81; Found: C, 67.24; H, 6.84; N, 7.73.

C. [2R-(2R*,3S*,6S*)]-N-t-Butyl- 2-[2-hydroxy-3-phenylmethyl- 4-aza-5-oxo-6-N (methylsulfonyl)amino- 7-(p-fluorophenylthio)]heptyl benzamide The subtitled compound was prepared substantially in accordance with the procedure detailed in Example 6 using 0.50 g (0.93 mmol) of the subtitled compound of Example 37B, 258 μL (1.86 mmol) of triethylamine and 86.4 μL (1.12 mmol) of methanesulfonyl chloride to provide a crude material. This material was purified using flash chromatography (eluent of 2% methanol in methylene chloride) to provide 0.46 g of a white solid. Yield: 81%. MS (FD): m/e 615($M^+$). Analysis for $C_{31}H_{38}FN_3O_5S_2$: Calcd: C, 60.47; H, 6.22; N, 6.82; Found: C, 60.73; H, 6.26; N, 6.88.

D. [2R-(2R*,3S*,6S*)]-N-t-Butyl- 2-[2-hydroxy-3-phenylmethyl- 4-aza-5-oxo-6-N(methylsulfonyl)amino- 7-(p-fluorophenylsulfinyl)]heptyl benzamide The subtitled compound was prepared substantially in accordance with the procedure detailed in Example 23D using 0.22 g (0.357 mmol) of the subtitled compound of Example 37C and 0.11 g (1 equiv.) of MCPBA to provide 0.23 g of a white solid. This solid was purified using flash chromatography (gradient eluent of 2.5–3% methanol in methylene chloride) to provide 0.13 g of a white solid. Yield: 57%. MS (FD): m/e 632($M^+$). Analysis for $C_{31}H_{38}FN_3O_6S_2$: Calcd: C, 58.94; H, 6.06; N, 6.65; Found: C, 59.12; H, 6.03; N, 6.81.

E. [2R-(2R*,3S*,6S*)]-N-t-Butyl- 2-[2-hydroxy-3-phenylmethyl- 4-aza-5-oxo-6-N(methylsulfonyl)amino- 7-(p-fluorophenylsulfonyl)]heptyl benzamide The subtitled compound was prepared substantially in accordance with the procedure detailed in Example 23D using 0.19 g (0.309 mmol) of the subtitled compound of Example 37C and 0.19 g (2 equiv.) of MCPBA to provide 0.22 g of crude material. This material was purified using flash chromatography (eluent of 2.5% methanol in methylene chloride) to provide 0.15 g of a white solid. Yield: 75%.

The subtitled compound was also isolated from the reaction mixture detailed in Example 37D. Yield: 60 mg. Analysis for $C_{31}H_{38}FN_3O_7S_2$: Calcd: C, 57.48; H, 5.91; N, 6.49; Found: C, 57.19; H, 5.86; N, 6.23.

EXAMPLE 38

A. [2R-(2R*,3S*,6S*)]-N-t-Butyl- 2-[2-hydroxy-3-phenylmethyl- 4-aza-5-oxo-6-N(t-butoxycarbonyl)amino- 7-pyrid-4-ylthio]heptyl benzamide The subtitled compound was prepared substantially in accordance with the procedure detailed in Example 1A using 0.20 g (0.587 mmol) of the subtitled compound of Preparation 1D, 0.18 g (0.587 mmol) of (2S)- 2-N(t-butoxycarbonyl)amino-3-pyrid-4-ylthiopropanoic acid, 0.79 g (0.587 mmol) of HOBT.H$_2$O and 0.12 g (0.587 mmol) of DCC to provide 0.39 g of a light yellow solid. This solid was purified using flash chromatography (eluent of 4% methanol in methylene chloride) to provide 0.19 g of a white solid. Yield: 53%. MS(FD): 621($M^+$).

B. [2R-(2R*,3S*,6S*)]-N-t-Butyl- 2-[2-hydroxy-3-phenylmethyl- 4-aza-5-oxo-6-amino -7-pyrid-4-ylthio]heptyl benzamide The subtitled compound was prepared substantially in accordance with the procedure detailed in Example 13B using 0.16 g (0.258 mmol) of the subtitled compound of Example 38A and 3 mL of trifluoroacetic acid to provide 0.14 g of a white solid. Yield: 59%. MS (FD): 521 ($M^+$).

C. [2R-(2R*,3S*,6S*)]-N-t-Butyl- 2-[2-hydroxy-3-phenylmethyl- 4-aza-5-oxo-6-N(methylsulfonyl)amino- 7-pyrid-4-ylthio]heptyl benzamide The subtitled compound was prepared substantially in accordance with the procedure detailed in Example 6 using 0.14 g (0.27 mmol) of the subtitled compound of Example 38B, 75 μL (0.54 mmol) of triethylamine and 25 μL (0.32 mmol) of methanesulfonyl chloride to provide 130 mg of a crude material. This material was purified using flash chromatography (gradient eluent of 4–6% methanol in methylene chloride) to provide 90 mg of a white solid. Yield: 56%. MS (FD): m/e 598(M$^+$). Analysis for $C_{30}H_{38}N_4O_5S_2$: Calcd: C, 60.18; H, 6.40; N, 9.36; Found: C, 60.43; H, 6.31; N, 9.07.

D. [2R-(2R*,3S*,6S*)]-N-t-Butyl- 2-[2-hydroxy-3-phenylmethyl- 4-aza-5-oxo-6-N (methylsulfonyl)amino- 7-pyrid-4ylsulfinyl]heptyl benzamide The subtitled compound was prepared substantially in accordance with the procedure detailed in Example 23D using 80 mg (0.134 mmol) of the subtitled compound of Example 38C and 40 mg (0.95 equiv.) of MCPBA to provide 0.80 g of a white solid. This solid was purified using flash chromatography (eluent of 4% methanol in methylene chloride) to provide 30 mg of a colorless oil. Yield: 36%.

E. [2R-(2R*,3S*,6S*)]-N-t-Butyl- 2-[2-hydroxy-3-phenylmethyl- 4-aza-5-oxo-6-N(methylsulfonyl)amino- 7-pyrid-4-ylsulfonyl]heptyl benzamide The subtitled compound was isolated from the reaction mixture detailed in Example 38D. Yield: 44 mg of a white solid.

EXAMPLE 39

A. [2R-(2R*,3S*,6S*)]-N-t-Butyl- 2-[2-hydroxy-3-phenylmethyl- 4-aza-5-oxo-6-N(t-butoxycarbonyl)amino- 7-N-(methyl)tetrazolylthio]heptyl benzamide The subtitled compound was prepared substantially in accordance with the procedure detailed in Example 1A using 1.12 g (3.3 mmol) of the subtitled compound of Preparation 1D, 1.0 g (3.3 mmol) of (2S)-2-N(t-butoxycarbonyl)amino-3-N-(methyl)tetrazolylthiopropanoic acid, 0.45 g (3.3 mmol) of HOBT.H$_2$O and 0.68 g (3.3 mmol) of DCC to provide 1.9 g of a white solid. This solid was purified using flash chromatography (eluent of 3% methanol in methylene chloride) to provide 1.1 g of a white solid. Yield: 52%. MS (FD): 626(M$^+$). Analysis for $C_{31}H_{43}N_7O_5S$: Calcd: C, 59.50; H, 6.93; N, 15.67; Found: C, 59.79; H, 7.03; N, 15.38.

B. [2R-(2R*,3S*,6S*)]-N-t-Butyl- 2-[2-hydroxy-3-phenylmethyl- 4-aza-5-oxo-6-amino- 7-N-(methyl)tetrazolylthio)] heptyl benzamide The subtitled compound was prepared substantially in accordance with the procedure detailed in Example 13B using 1.1 g (1.76 mmol) of the subtitled compound of Example 39A and 5 mL of trifluoroacetic acid to provide 0.87 g of crude material. This material was purified using flash chromatography (gradient eluent of 4–6% methanol in methylene chloride) to provide 0.58 g of the desired subtitled compound. Yield: 63%. MS(FD): 526(M$^+$).

C. [2R-(2R*,3S*,6S*)]-N-t-Butyl- 2-[2-hydroxy-3-phenylmethyl- 4-aza-5-oxo-6-N(methylsulfonyl)amino- 7-N-(methyl)tetrazolylthio)]heptyl benzamide.

The subtitled compound was prepared substantially in accordance with the procedure detailed in Example 6 using 0.58 g (1.10 mmol) of the subtitled compound of Example 39B, 305 μL (2.20 mmol) of triethylamine and 102 μL (1.32 mmol) of methanesulfonyl chloride to provide 0.61 g of a crude material. This material was purified using flash chromatography (eluent of 3% methanol in methylene chloride) to provide 0.48 g of a white solid. Yield: 73%. MS (FD): m/e 604(M$^+$). Analysis for $C_{27}H_{37}N_7O_5S_2$: Calcd: C, 53.71; H, 6.18; N, 16.24; Found: C, 53.64; H, 6.18; N, 16.09.

D. [2R-(2R*,3S*,6S*)]-N-t-Butyl- 2-[2-hydroxy-3-phenylmethyl- 4-aza-5-oxo-6-N(methylsulfonyl)amino- 7-N-(methyl)tetrazolylsulfinyl)] heptyl benzamide The subtitled compound was prepared substantially in accordance with the procedure detailed in Example 23D using 0.15 g (0.248 mmol) of the subtitled compound of Example 39C and 0.078 g (1 equiv.) of MCPBA to provide 0.17 g of crude material. This material was purified using flash chromatography (gradient eluent of 2.5–3% methanol in methylene chloride) to provide 0.70 g of the desired subtitled compound. Yield: 47%. MS (FD): m/e 620(M$^+$).

EXAMPLE 40

[2R-(2R*,3S*,6S*)]-N-t-Butyl- 2-[2-hydroxy-3-phenylmethyl- 4-aza-5-oxo-6-amino- 7-phenyl]heptyl benzamide The subtitled compound was prepared substantially in accordance with the procedure detailed in Example 1A using 0.18 g (0.52 mmol) of the subtitled compound of Preparation 1D, 0.10 g (0.52 mmol) of (2S)-2-N(formyl)amino-3-phenyl propanoic acid, 0.07 g (0.52 mmol) of HOBT.H$_2$O and 0.11 g (0.52 mmol) of DCC to provide 0.26 g of a white solid. This solid was purified using flash chromatography (eluent of 2% methanol in methylene chloride) to provide 0.17 g of a white solid. Yield: 63%. MS (FD): 516 (M$^+$).

EXAMPLE 41

[2R-(2R*,3S*,6S*)]-N-t-Butyl- 2-[2-hydroxy-3-phenylmethyl- 4-aza-5-oxo-6-N(trifluoromethylcarbonyl)amino-7-benzyloxycarbonyl]heptyl benzamide To a solution of 0.13 g (0.24 mmol) of the subtitled compound of Example 1B in 3 mL of absolute ethanol, was added 46 mL (0.357 mmol) of S-ethyl trifluorothioacetate. The resultant reaction mixture was allowed to react at room temperature for approximately two hours and an additional 3 mL of ethanol and 0.5 mL of S-ethyl trifluorothioacetate was added. When the reaction was substantially complete, as indicated by NMR, the mixture was concentrated under reduced pressure to provide 0.13 g of a white solid. This solid was further purified using column chromatography (Rainin C18 column, eluent of methylene chloride) to provide 80 mg of a white solid. Yield: 53%.

EXAMPLE 42

[2R-(2R*,3S*,6S*)]-N-t-Butyl- 2-[2-hydroxy-3-phenylmethyl- 4-aza-5-oxo-6-N(trifluoromethylcarbonyl)amino-7-naphth-2-ylthio] heptyl benzamide The subtitled compound was prepared substantially in accordance with the procedure detailed in Example 41 using 0.12 g (0.21 mmol) of the subtitled compound of Example 15B and S-ethyl trifluorothioacetate in 4 mL of ethanol to provide 0.13 g of a white solid. This solid was purified using preparatory HPLC (eluent of acetonitrile and water containing ammonium acetate) to provide 70 mg of the desired titled compound. Yield: 50%. MS (FD): 516(M$^+$).

As noted above, the compounds of the present invention are useful for inhibiting HIV protease, which is an enzyme associated with viral component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method of inhibiting HIV replication comprising administering to an HIV infected cell, a cell susceptible to HIV infection or a primate in need thereof, an effective amount of a compound of formula I or a pharmaceutically acceptable salt thereof.

The term "effective amount" as used herein, means an amount of a compound of the present invention which is capable of inhibiting the HIV protease mediated viral component production and assembly. The HIV protease inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

FORMULATION 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight |
|---|---|
| Active ingredient | 0.25 |
| Methanol | 25.75 |
| Propellane 2 | 70.00 |
| (Chlorofluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

|  |  |
|---|---|
| Active ingredient | 60 mg |
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of the present invention to inhibit HIV protease.

As used herein, the abbreviations are defined as follows:
BSA - bovine serum albumin
BOC - t-butyloxycarbonyl
BrZ - 2-bromobenzyloxycarbonyl
2-ClZ - 2-chlorobenzyloxycarbonyl
DCC - dicyclohexylcarbodiimide
DIEA - diisopropylethylamine
DTT - dithiothreitol
EDTA - ethylenediaminetetraacetic acid
FITC - fluorescein isothiocarbamyl
HEPES - 4-(2-hydroxyethyl)-1-piperazine-ethanesulfonic acid
MES - 4 morpholineethanesulfonic acid
PAM - phenylacetimidomethyl
TAPS - 3-[tris(hydroxymethyl)methyl]amino-1-sulfonic acid
TRIS - tris(hydroxymethyl)aminomethane
TOS - p-toluenesulfonyl (tosyl)

I. Preparation of Protease and Gag Fractions

A. Culture of E. coli K12 L507/pHP10D

Lyophils of E. coli K12 L507/pHP10D were obtained from the Northern Regional Research Laboratory, Peoria, Ill. 61604, under the accession number NRRL B-18560 (deposited Nov. 14, 1989). The lyophils were decanted into tubes containing 10 mL LB medium (10 g Bacto-trypone, 5 g Bacto-yeast extract, and 10 g sodium chloride per liter; the pH was adjusted to 7.5 and incubated at 32° C., overnight).

A small portion of the overnight culture was placed on LB-agar (LB medium with 15 g/L Bacto-agar) plates containing 12.5 µg/mL tetracycline in a manner so as to obtain a single colony isolate of E. coli K12 L507/pHP10D. The single colony obtained was inoculated into 10 mL of LB medium containing 12.5 µg/mL tetracycline and incubated overnight at 32° C. with vigorous shaking. The 10 mL overnight culture was inoculated into LB medium containing 12.5 µg/mL tetracycline and incubated at 32° C. with vigorous shaking until the culture reached mid-log phase.

B. Culture of E. coli K12 L507/pHGAG

Lyophils of E. coli K12 L507/pHGAG were obtained from the NRRL under the accession number NRRL B-18561 (deposited Nov. 14, 1989). A purified colony of E. coli K 12 L507/pHGAG was isolated, and used as an inoculum for a culture which was grown to mid-log phase in substantial accordance with the teaching of Step A, above, for E. Coli K12 L507/pHP10D.

C. Preparation of Protease Fraction

A culture of E. coli K12 L507/pHP10D was grown to mid-log phase at 32° C. in LB media containing 12.5 µg/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000×g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluted with a gradient eluent of 0–1.0M sodium chloride in Buffer A over 120 min. Enzymatic activity was measured by HPLC using the synthetic peptide SQNYPIV as described in Margolin et al., *Biochem. Biophys. Res. Commun.*, 167, 554–560 (1990); the production of the p1 peptide (SQNY) was measured.

The active fractions were combined, made 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M sodium chloride in Buffer A over 40 min. The column was washed isocratically in Buffer A containing 0.45M sodium chloride for 30 min.

The active fractions were combined and concentrated to 200 µL using an Amicon stirred cell and a YM-10 membrane and then the protease was applied to a Superose 6 size exclusion column equilibrated in Buffer A containing 0.1M sodium chloride. The column was washed isocratically in this buffer at a flow rate of 0.5 mL/min, following which the HIV protease was eluted as a single peak.

QAE-Sepharose, and hexyl agarose were purchased from Sigma Chemical Company. Superose 6 and MonoS were were purchased from Pharmacia. Buffers and reagents were obtained from Sigma.

D. Preparation of Gag Fraction

In an analogous manner, a culture of E. coli K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis buffer was comprised of 50 mM Tris-HCl (pH 7.8), 5 mM EDTA, 1 mM DTT, 100 mM NaCl, 1 µg/mL E64 and 2 µg/mL aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000×g. The supernatant, which contains the unprocessed gag protein, was partially purified by size exclusion chromatography on a Sephadex G-50 column and stored at −20° C. in 50% glycerol and lysis buffer.

II. Preparation of Substrate: $N^\alpha$-Biotin-GlY-Ser-Gln-Asn-Tyr-Pro-Ile-Val-Gly-Lys ($N^\epsilon$-FITC)-OH SEQ ID NO:1.

A. Preparation of $N^\alpha$-Biotin-Gly-Ser-Gln-Asn-Tyr-Pro-Ile-Val-Gly-Lys-OH SEQ ID NO:3.

The protected peptide-resin $N^\alpha$-Boc-Gly-Ser-Gln-Asn-Tyr(BrZ)-Pro-Ile-Val-Gly-Lys(2-ClZ)-OCH$_2$-PAM-resin SEQ ID NO:2. was synthesized on an Advanced Chemtech Model 200 peptide synthesizer at 1.5 mmol scale using the standard double-couple protocol. The amino terminal Boc group was removed with 50% trifluoroacetic acid in methylene chloride and the resulting resin neutralized with 5% di(isopropyl)ethylamine (DIEA) in methylene chloride. Then, 1.1 g (4.5 mmol) of biotin in 20 mL of dimethylsulfoxide was added to the peptide resin, followed by 4.5 mmol of dicyclohexylcarbodiimide (DCC) in 9 mL of methylene chloride. The resulting reaction mixture was diluted to 40 mL total volume using 11 mL methylene chloride, and then allowed to react for approximately 5 hours. The reaction solution was concentrated, the resin washed sequentially with dimethylsulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. Deprotection

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL of diethylether. The peptide was then solubilized in 50% aqueous acetic acid, frozen and lyophilized to provide 2.14 g.

C. Purification

The crude $N^\alpha$-Biotin-Gly-Ser-Gln-Asn-Tyr-Pro-Ile-Val-Gly-Lys-OH SEQ ID NO: 3. was dissolved in 200 mL of a 5% acetonitrile (aqueous) solution containing 0.1% trifluoroacetic acid and then filtered through a 0.22 micron filter. The resulting solution was applied to a 2.2×25 cm. reverse phase column of octadecyl-silica (Vydac C-18) which had been equilibrated with the same buffer. The peptide was eluted using an 855 minute linear gradient of 7.5–25% acetonitrile, at 2 mL/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated $N^\alpha$-Biotin-Gly-Ser-Gln-Asn-Tyr-Pro-Ile-Val-Gly-Lys-OH SEQ ID NO:3. gave the following ratios: Asn 1.1; Set 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. Labeling

The purified peptide was labeled with a fluorescent marker at the C-terminal end for use in the Pandex assay. $N^\alpha$-Biotin-Gly-Ser-Gln-Asn-Tyr-Pro-Ile-Val-Gly-Lys-OH SEQ ID NO:3. (1.206 g, 0.936 mmol) was dissolved in 100 mL of 0.1M sodium borate, pH 9.5. Then, a solution of 3 g (7.7 mmol) of fluorescein isothiocyanate in 15 mL dimethyl sulfoxide was added to the reaction mixture in 10 equal portions over two hours. The resulting mixture was allowed to react for one hour after the final addition. The solution was adjusted to pH 3 using 5N hydrochloric acid, resulting in the formation of a precipitate which was removed by centrifugation.

The peptide solution was then adjusted to pH 7.8 using 5N sodium hydroxide and then diluted to 200 mL total volume by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 mL/minute, with collection of fractions. Analytical HPLC was used to analyze the fractions. The fractions containing the desired product were then combined, frozen and lyophilized to provide 190.2 mg (12%).

Amino acid analysis of the purified peptide gave the following: Ash 1.1; Ser 1.0; Gln 1.1: Pro 1.1; Gly 2.1; Val 0.8; Ile 0.8; Tyr 1.1; Lys 1.0; in agreement with theory. Fast-atom bombardment mass spectrometry gave amolecular ion mass peak of 1678, in agreement with theory.

E. Fluorescence HIV-1 Protease Inhibitor Assay

The following buffers and solutions are used in the Fluorescence HIV-1 Protease Inhibitor Assay:

| | |
|---|---|
| MES-ALB Buffer: | 0.05M 4-morpholineethane sulfonic acid, pH 5.5 |
| | 0.02M NaCl |
| | 0.002M EDTA |
| | 0.001M DTT |
| | 1.0 mg/mL BSA |

-continued

| | |
|---|---|
| TBSA Buffer: | 0.02M TRIS<br>0.15M NaCl<br>1.0 mg/mL BSA |
| Avidin Coated Beads Solution: | 0.1% solution of Fluoricon Avidin Assay Particles (Avidin conjugated to solid polystyrene beads, 0.6–0.8 microns in diameter in TBSA Buffer |
| Enzyme Solution: | 27 IU/mL of purified HIV-1 protease in MES-ALB buffer (1 IU equals the amount of enzyme required to hydrolyze 1 μmole of substrate per minute at 37° C. |

To each well of a round bottom, 96-well plate is added 20 μL of the Enzyme Solution followed by 10 μL of the compound to be evaluated in a 20% aqueous dimethylsulfoxide solution. Purified HIV-1 protease was obtained as described above. The resulting solution is incubated for one hour at room temperature and then 20 μL of a solution containing the substrate, $N^\alpha$-Biotin-Gly-Ser-Gln-Asn-Tyr-Pro-Ile-Val-Gly-Lys($N^\epsilon$-FITC)-OH, SEQ ID NO:1. in MES-ALB buffer (1.5 μl/mL) is added to each well. The solutions are then incubated for 16 hours at room temperature and then each well is diluted with 150 μL of MES-ALB buffer.

To each well of a second round bottom, 96-well Pandex plate is added 25 uL of the Avidin Coated Beads Solution. Then, to each well is added 25 μL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The $IC_{50}$ results obtained in the Fluorescence Assay for the compounds of the present invention are set forth below in Table 1. All values have been normalized to a positive control which is [1S-(1R*,4R*,5S*)]-N-(1-( 2-amino-2-oxoethyl)-2-oxo-3-aza-4-phenylmethyl-5-hydroxy-6-( 2-(1-t-butylamino-1-oxomethyl)phenyl)hexyl)-2-quinolinyl carboxamide.

TABLE 1

| Inhibitory Activity of Formula I Compounds | |
|---|---|
| Example No. | Fluorescence Assay $IC_{50}$ in ng/mL |
| Control | 1.0 |
| 1A | >1000* |
| 1B | — |
| 1C | 33 |
| 1D | — |
| 2 | 265 |
| 3 | 342 |
| 4 | 200 |
| 5 | 5.6 |
| 6 | 16 |
| 7 | 71 |
| 8A | 2.3 |
| 8B | — |
| 9 | 9 |
| 10 | 2.7 |
| 11 | 1.7 |
| 12 | 17 |
| 13A | — |
| 13B | $IC_5$ = 1000* |
| 13C | 129 |

TABLE 1-continued

| Inhibitory Activity of Formula I Compounds | |
|---|---|
| Example No. | Fluorescence Assay $IC_{50}$ in ng/mL |
| 14 | 26 |
| 15A | >1000 |
| 15B | 127 |
| 16A | 6.5 |
| 16B | 0.12 |
| 17A | 0.71 |
| 17B | 0.13 |
| 18A | 7.4 |
| 18B | 34 |
| 19A | $IC_3$ = 1000* |
| 19B | $IC_{16}$ = 1000* |
| 19C | 2.2 |
| 19D | 1.4 |
| 19E | 3.0 |
| 20A | 73 |
| 20B | $IC_8$ = 1000* |
| 20C | 2.9 |
| 21 | $IC_{45}$ = 1000* |
| 22A | $IC_3$ = 2000* |
| 22B | $IC_3$ = 1000* |
| 22C | 11.3 |
| 22D | 1.6 |
| 22E | 0.6 |
| 23A | — |
| 23B | — |
| 23C | 16.8 |
| 23D | 0.8 |
| 23E | 2.7 |
| 24A | 2.3 |
| 24B | 0.13 |
| 24C | 0.16 |
| 25 | >1000* |
| 26 | $IC_{45}$ = 1000* |
| 27A | — |
| 27B | — |
| 28 | — |
| 29A | — |
| 29B | — |
| 29C | 221 |
| 30 | 12 |
| 31A | $IC_8$ = 1000* |
| 31B | — |
| 31C | $IC_{30}$ = 1000* |
| 32 | $IC_{12}$ = 1000* |
| 33 | 44 |
| 34 | 1.3 |
| 35 | 0.7 |
| 36 | — |
| 37A | >1000* |
| 37B | 2866 |
| 37C | 1.1 |
| 37D | 0.10 |
| 37E | — |
| 38A | — |
| 38B | — |
| 38C | — |
| 38D | — |
| 38E | — |
| 39A | >1000* |
| 39B | — |
| 39C | 8.8 |
| 39D | 0.87 |
| 40 | $IC_8$ = 1000* |
| 41 | $IC_{52}$ = 20* |
| 42 | 0.74 |

*the concentration of the compound was not increased above the stated concentration.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /label=Modified-site
            / note="The alpha amino group of glycine at position one is biotinylated."

( i x ) FEATURE:
        ( A ) NAME/KEY: Modified-site
        ( B ) LOCATION: 9..10
        ( D ) OTHER INFORMATION: /label=Modified-site
            / note="The epsilon amino group of lysine at position 10 of the peptide has been derivatized with FITC."

( x i ) SEQUENCE DESCRIPTION: SEQ ID NO:1:

```
Gly  Ser  Gln  Asn  Tyr  Pro  Ile  Val  Gly  Lys
 1              5                         10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /label=Modified-site
            / note="The alpha amino of glycine at position one with t- butoxycarbonyl."

( i x ) FEATURE:
        ( A ) NAME/KEY: Active-site
        ( B ) LOCATION: 5..6
        ( D ) OTHER INFORMATION: /label=modified-site
            / note="2-bromobenzyloxycarbonyl is used as a side chain protecting group in the solid phase preparation of the peptide."

( i x ) FEATURE:
        ( A ) NAME/KEY: Modified-site
        ( B ) LOCATION: 9..10
        ( D ) OTHER INFORMATION: /label=modified-site
            / note="The epsilon amino group of the lysine is derivatized with 2-chlorobenzyloxycarbonyl. The carboxy terminus is linked to a PAM resin."

( x i ) SEQUENCE DESCRIPTION: SEQ ID NO:2:

```
Gly  Ser  Gln  Asn  Tyr  Pro  Ile  Val  Gly  Lys
 1              5                         10
```

( 2 ) INFORMATION FOR SEQ ID NO:3:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Modified-site
  (B) LOCATION: 1..2
  (D) OTHER INFORMATION: /label=modified-site
       /note="The alpha amino group of glycine at position one is biotinylated."

(xi) SEQUENCE DESCRIPTION: SEQ ID NO:3:

Gly Ser Gln Asn Tyr Pro Ile Val Gly Lys
 1           5                       10

We claim:

1. A compound of formula I

[structure I]

wherein:

Z is hydrogen, formyl, carbamoyl, $C_2$–$C_6$ alkanoyl, $C_1$–$C_4$ alkoxycarbonyl, —C(O)CF$_3$ or —S(O)$_2$—R, where R is $C_1$–$C_6$ alkyl, amino, trifluoromethyl, $C_1$–$C_4$ alkylamino, di ($C_1$–$C_4$) alkylamino, aryl, aryl ($C_1$–$C_4$) alkyl, heterocycle, unsaturated heterocycle or $C_5$–$C_7$ cycloalkyl;

$R^1$ is aryl, $C_5$–$C_7$ cycloalkyl or —S—$R^{1x}$, where $R^{1x}$ is aryl or $C_5$–$C_7$ cycloalkyl;

$R^2$ is an amino acid side chain, —(CH$_2$)$_y$—X—$R^{2a}$, cyano ($C_1$–$C_4$)alkyl or —(CH$_2$)$_y$—S(O)$_w$—[1-N($R^{2c}$)-tetrazol-5-yl], where
  y is 0, 1, 2 or 3;
  X is a bond, divalent ($C_2$–$C_4$) alkenyl, divalent ($C_2$–$C_4$)alkynyl, —C(O)—O—, —O—C(O)—, —C(O)—NR$^{2b}$—, —NR$^{2b}$—C(O)—, —NR$^{2b}$—, —C(O)—, —O—, or —S(O)$_w$—,
  w is 0, 1 or 2;
  $R^{2a}$ is $C_1$–$C_6$ alkyl, aryl, unsaturated heterocycle, heterocycle, aryl ($C_1$–$C_4$)alkyl, unsaturated heterocycle ($C_1$–$C_4$)alkyl or heterocycle ($C_1$–$C_4$) alkyl;
  $R^{2b}$ is hydrogen or $C_1$–$C_4$ alkyl;
  $R^{2c}$ is hydrogen, $C_1$–$C_6$ alkyl, aryl, unsaturated heterocycle, aryl ($C_1$–$C_4$) alkyl or unsaturated heterocycle ($C_1$–$C_4$) alkyl;

Y is aryl or unsaturated heterocycle;
$R^3$ is a group having the structure:

1) —C(O)—NR$^4$R$^4$,

2) [structure 2]

3) [structure 3],

4) —N(R$^5$)—C(O)—R$^6$,

5) —N(R$^4$)—C(O)—NR$^4$R$^4$, or

6) [structure 6];

where:
p is 4 or 5;
l is 3, 4 or 5;
$R^4$ at each occurrence is independently hydrogen, $C_1$–$C_6$ alkyl or hydroxy ($C_1$–$C_4$) alkyl;
$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy ($C_1$–$C_4$) alkyl, carboxy, $C_1$–$C_4$ alkoxycarbonyl, carbamoyl, N—($C_1$–$C_4$) alkylcarbamoyl, aryl, heterocycle or unsaturated heterocycle;

with the proviso that when Z is hydrogen, formyl, carbamoyl, $C_2$–$C_6$ alkanoyl or $C_1$–$C_4$ alkoxycarbonyl; $R^2$ is an amino acid side chain or —(CH$_2$)$_y$—X—$R^{2a}$, where y is 0, 1, 2 or 3; X is a bond, —C(O)—O— or —C(O)—NR$^{2b}$—; $R^{2b}$ is hydrogen; and $R^{2a}$ is aryl, heterocycle or unsaturated heterocycle, then $R^1$ must be aryl or $C_5$–$C_7$ cycloalkyl; or a pharmaceutically acceptable salt thereof.

2. A compound according to claim 1 wherein:
$R^1$ is phenyl;
Y is phenyl; and
$R^3$ is —C(O)NH(t-butyl); or a pharmaceutically acceptable salt thereof.

3. A compound according to claim 2 of formula IA

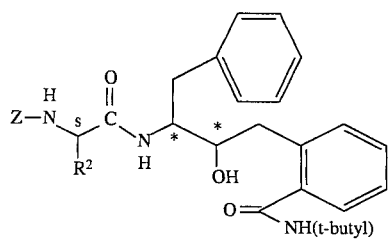

wherein:

Z is —S(O)₂—R, where
R is aryl, aryl (C₁–C₄)alkyl or C₅–C₇ cycloalkyl; and
R² is —CH₂CN, —CH(CH₃)₂ or —CH₂—C(O)NH₂; or a pharmaceutically acceptable salt thereof.

4. A compound according to claim 2 of formula IB

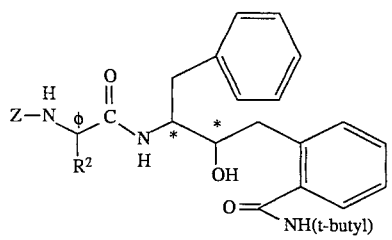

wherein:

Z is —C(O)CF₃, C₂–C₆ alkanoyl or —S(O)₂—R, where R is C₁–C₆ alkyl;
R² is —(CH₂)ᵧ—X—R²ᵃ, where:
y is 1;
X is —C(O)—O—, —C(O)—NR²ᵇ— or —S(O)ᵥᵥ—; and
R²ᵃ is aryl, heterocycle, aryl (C₁–C₄) alkyl heterocycle (C₁–C₄) alkyl or N— (C₁–C₄) alkyltetrazolyl; with the provisos that:
(1) when X is —C(O)—0— or —C(O)—NR²ᵇ—, then the asymmetric center denoted ϕ is an "R"; and
(2) when X is —S—, —S(O)— or —S(O)₂—, then the asymmetric center denoted ϕ is an "S"; or a pharmaceutically acceptable salt thereof.

5. A compound according to claim 4 wherein:

Z is ethanoyl —C(O)CF₃, or —S(O)₂—CH₃; and
R²ᵃ is phenyl, p-fluorophenyl, phenylmethyl, naphthyl, naphthylmethyl, pyridyl, quinolinyl, quinolinylmethyl or N-methyltetrazolyl; or a pharmaceutically acceptable salt thereof.

6. A compound according to claim 5 which is [2R—(2R*, 3S*,6S*)]-N-t-butyl-2-[2-hydroxy-3-phenylmethyl-4-aza-5-oxo-6-N(ethanoyl)amino-7-naphth- 2-ylsulfonyl]heptyl benzamide or a pharmaceutically acceptable salt thereof.

7. A compound according to claim 5 which is [2R-(2R*, 3S*,6S*)]-N-t-butyl-2-[2-hydroxy-3-phenylmethyl-4-aza-5-oxo-6-N(methylsulfonyl)amino- 7-naphth-2-ylthio]heptyl benzamide or a pharmaceutically acceptable salt thereof.

8. A compound according to claim 5 which is [2R-(2R*,3S*,6S*)]-N-8-butyl- 2- [2-hydroxy-3-phenylmethyl-4-aza- 5-oxo-6-N(methylsulfonyl)amino- 7-naphth-2-ylsulfonyl]heptyl benzamide or a pharmaceutically acceptable salt thereof.

9. A compound according to claim 5 which is [2R-(2R*, 3S*,6S*)]-N-t-butyl-2-[2-hydroxy-3-phenylmethyl-4-aza-5-oxo-6-N(methylsulfonyl)amino-7phenylsulfinyl]heptyl benzamide or a pharmaceutically acceptable salt thereof.

10. A compound according to claim 5 which is [2R-(2R*, 3S*,6S*)] -N-8-butyl- 2- [2-hydroxy-3-phenylmethyl-4-aza- 5-oxo-6-N (methylsulfonyl) amino- 7-quinolin-2-ylsulfonyl]heptyl benzamide or a pharmaceutically acceptable salt thereof.

11. A compound according to claim 5 which is [2R-(2R*, 3S*,6S*)] -N-t-butyl-2-[2-hydroxy-3-phenylmethyl-4-aza-5-oxo-6-N(ethanoyl)amino- 7-quinolin-2-ylsulfinyl]heptyl benzamide or a pharmaceutically acceptable salt thereof.

12. A compound according to claim 5 which is [2R-(2R*, 3S*,6S*)] -N-t-butyl-2-[2-hydroxy-3-phenylmethyl-4-aza-5-oxo-6-N(ethanoyl)amino- 7-quinotin-2-ylsulfonyl] heptyl benzamide or a pharmaceutically acceptable salt thereof.

13. A compound according to claim 5 which is [2R-(2R*, 3S*,6S*)] -N-t-butyl- 2-[2-hydroxy-3-phenylmethyl-4-aza-5-oxo-6-N(methylsulfonyl)amino- 7-(p-fluorophenylsulfinyl)] heptyl benzamide; or a pharmaceutically acceptable salt thereof.

14. A compound according to claim 3 which is [2R-(2R*, 3S*,6S*)]-N-S-butyl-2-[2-hydroxy-3-phenylmethyl-4-aza-5-oxo- 6-N(naphth-1-ylethyl-sulfonyl)amino-7-carbamoyl] heptyl benzamide or a pharmaceutically acceptable salt thereof.

15. A pharmaceutical formulation comprising one or more pharmaceutically acceptable carriers, diluents or excipients and a compound of claim 1.

16. A pharmaceutical formulation according to claim 15 where the compound is one wherein:

R¹ is phenyl;
Y is phenyl; and
R³ is —C(O)NH(t-butyl); or a pharmaceutically acceptable salt thereof.

17. A pharmaceutical formulation according to claim 16 where the compound is of formula IA

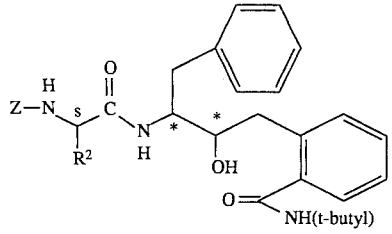

wherein:

Z is —S(O)₂—R, where
R is aryl, aryl (C₁–C4)alkyl or C₅–C₇ cycloalkyl; and
R² is —CH₂CN, —CH (CH₃)₂ or —CH₂—C (O)NH₂; or a pharmaceutically acceptable salt thereof.

18. A pharmaceutical formulation according to claim 16 where the compound is of formula IB

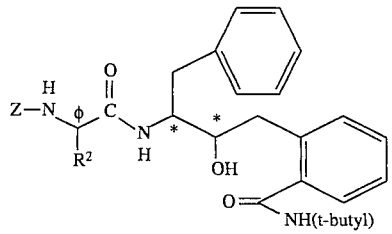

wherein:

Z is —C(O)CF₃, C₂–C₆ alkanoyl or —S(O)₂—R, where R is C₁–C₆ alkyl;
R² is —(CH₂)ᵧ—X—R²ᵃ, where:
y is 1;
X is —C(O)—O—, —C(O) —NR²ᵇ— or —S(O)ᵥᵥ—; and $R^{2a}$ is aryl, heterocycle, aryl ($C_1$–$C_4$) alkyl heterocycle ($C_1$–$C_4$) alkyl or N—($C_1$–$C_4$) alkyltetrazolyl; with the provisos that:

(1) when X is —C(O)—O— or —C(O)—$NR^{2b}$—, then the asymmetric center denoted $\phi$ is an "R"; and (2) when X is —S—, —S(O)— or —S(O)$_2$—, then the asymmetric center denoted $\phi$ is an "S"; or a pharmaceutically acceptable salt thereof.

19. A pharmaceutical formulation according to claim 18 where the compound is one wherein:

Z is ethanoyl, —C(O)CF$_3$, or —S(O)$_2$—CH$_3$; and $R^{2a}$ is phenyl, p-fluorophenyl, phenylmethyl, naphthyl, naphthylmethyl, pyridyl, quinolinyl, quinolinylmethyl or N-methyltetrazolyl; or a pharmaceutically acceptable salt thereof.

20. A pharmaceutical formulation according to claim 19 where the compound is [2R-(2R*,3S*,6S*)]-N-t-butyl-2-[ 2-hydroxy-3-phenylmethyl-4-aza-5-oxo-6-N (ethanoyl) amino-7-naphth-2-ylsulfonyl] heptyl benzamide or a pharmaceutically acceptable salt thereof.

21. A pharmaceutical formulation according to claim 19 where the compound is [2R-(2R*, 3S*,6S*)]-N-t-butyl-2-[2-hydroxy- 3-phenylmethyl-4-aza-5-oxo- 6-N(methylsulfonyl)amino-7-naphth-2-ylthio] heptyl benzamide or a pharmaceutically acceptable salt thereof.

22. A pharmaceutical formulation according to claim 19 where the compound is [2R-(2R*,3S*, 6S*)]-N-t-butyl-2-[2-hydroxy-3-phenylmethyl- 4-aza-5-oxo-6N(methylsulfonyl)amino- 7-naphth-2-ylsulfonyl] heptyl benzamide or a pharmaceutically acceptable salt thereof.

23. A pharmaceutical formulation according to claim 19 where the compound is [2R-(2R*,3S*, 6S*)]-N-t-butyl-2-[2-hydroxy-3-phenylmethyl- 4-aza-5-oxo-6-N(methylsulfonyl)amino- 7-phenylsulfinyl] heptyl benzamide or a pharmaceutically acceptable salt thereof.

24. A pharmaceutical formulation according to claim 19 where the compound is [2R-(2R*,3S*, 6S*)]-N-t-butyl-2-[ 2-hydroxy-3-phenylmethyl- 4-aza-5-oxo-6-N(methylsulfonyl)amino-7-quinolin- 2-ylsulfonyl]heptyl benzamide or a pharmaceutically acceptable salt thereof.

25. A pharmaceutical formulation according to claim 19 where the compound is [2R-(2R*,3S*, 6S*2]-N-t-butyl-2-[2-hydroxy-3-phenylmethyl- 4-aza-5-oxo-6-N(ethanoyl)amino- 7-quinolin-2-ylsulfinyl] heptyl benzamide or a pharmaceutically acceptable salt thereof.

26. A pharmaceutical formulation according to claim 19 where the compound is [2R-(2R*,3S*, 6S*)]-N-t-butyl-2-[2-hydroxy-3-phenylmethyl- 4-aza-5-oxo-6-N(ethanoyl) amino-7-quinolin- 2-ylsulfonyl] heptyl benzamide or a pharmaceutically acceptable salt thereof.

27. A pharmaceutical formulation according to claim 19 where the compound is [2R-(2R*,3S*, 6S*)]-N-t-butyl-2-[2-hydroxy-3-phenylmethyl- 4-aza-5-oxo-6-N(methylsulfonyl)amino-7- (p-fluorophenylsulfinyl)] heptyl benzamide; or a pharmaceutically acceptable salt thereof.

28. A pharmaceutical formulation according to claim 17 where the compound is [2R-(2R*,3S*, 6S*)]-N-t-butyl-2-[2-hydroxy-3-phenylmethyl- 4-aza-5-oxo-6-N(naphth- 1-yl-ethyl-sulfonyl)amino-7-carbamoyl]heptyl benzamide or a pharmaceutically acceptable salt thereof.

\* \* \* \* \*

UNITED STATES PATENT AND TRADEMARK OFFICE
CERTIFICATE OF CORRECTION

PATENT NO. : 5,554,653    Page 1 of 4
DATED     : September 10, 1996
INVENTOR(S) : Hui, et al It is certified that error appears in the above-identified patent and that said Letters Patent is hereby corrected as shown below:

Column 1, line 41, "Hitsuya," should read --Mitsuya,--.
Column 1, line 56, "Are" should be lower-cased and read as --are--.
Column 4, line 11, "halo(Cl-$C_4$)alkyl" should read --halo($C_1$-$C_4$)alkyl--.
Column 4, line 17, "hydroxy($C_1C_4$)alkyl" should read --hydroxy($C_1$-$C_4$)alkyl--.
Column 4, line 43, "sec-butylamino" should read --*sec*-butylamino--.
Column 5, line 7, " N-{$C_1$-$C_4$)alkylcarbamoyl" should read --N-($C_1$-$C_4$)alkylcarbamoyl--.
Column 5, line 40, "halo($C_1C_4$)alkyl," should read --halo($C_1$-$C_4$)alkyl,--.
Column 6, line 66, "Thronine" should read --Threonine--.
Column 7, line 63, "8-butyldimethylsilyl," should read --t-butyldimethylsilyl,--.
Column 10, line 16, "N-8-butyl-2" should read --N-t-butyl-2--.
Column 10, line 31, "N-8-Butyl-2" should read --N-t-Butyl-2--.
Column 10, line 47, "N-8-butyl-2" should read --N-t-butyl-2--.
Column 10, line 50, "N-8-butyl-2" should read --N-t-butyl-2--.
Column 13, line 55, "(HOBT.$H_2$O)." should read --(HOBT·$H_2$O).--.
Column 16, line 11, "HOBT.$H_2$O." should read --HOBT·$H_2$O.--.
Column 16, line 51, "HOBT.$H_2$O." should read --HOBT·$H_2$O.--.

Column 18, line 17, "2M" should read --2$\underline{N}$--.
Column 18, line 45, "0.2N" should read --0.2$\underline{N}$--.
Column 18, line 17, "1.0N" should read --1.0$\underline{N}$--.
Column 18, line 50, "—289°—26°" should read -- —289.26°--.
Column 18, line 52, second occurrence of "6 Hz, 1H", "should read --6 Hz, 1H),--.
Column 18, line 54, "5.56 d," should read --5.56 (d,--.
Column 18, line 60, "N-t-Butyl-2-(B" should read --N-t-Butyl-2-(3--.
Column 19, line 4, "1N" should read --1$\underline{N}$--.
Column 19, line 47, "(HOBT.$H_2$O)" should read --(HOBT·$H_2$O)--.
Column 20, line 12, "6R*)1" should read --6R*)]--.
Column 20, line 41, "{m, 1H)" should read --(m, 1H)--.

UNITED STATES PATENT AND TRADEMARK OFFICE
CERTIFICATE OF CORRECTION

PATENT NO. : 5,554,653
DATED : September 10, 1996
INVENTOR(S) : Hui, et al

It is certified that error appears in the above-identified patent and that said Letters Patent is hereby corrected as shown below:

Column 21, line 8, "10N" should read --10$\underline{N}$--.
Column 21, line 46, "amine" should read --amino--.
Column 21, line 60, "$C_{36}H_{41}N_5OS$-" should read --$C_{36}H_{41}N_5O_5$---.
Column 22, line 5, "HOBT.H$_2$O" should read --HOBT·H$_2$O--.
Column 22, line 11, "1H ," should read --1H),--.
Column 22, line 12, "(hr. s, 1H )," should read --(br.s, 1H),--.

Column 22, line 36, "(hr. s, 1H)," should read --(br.s, 1H),--.
Column 22, line 51, "1N" should read --1$\underline{N}$--.
Column 23, line 46, "HOBT-H$_2$O" should read --HOBT·H$_2$O--.
Column 23, line 54, "(hr." should read --(br.--.
Column 23, line 55, "(H$^+$)." should read --(M$^+$).--.
Column 23, line 66, "HOBT-H$_2$O" should read --HOBT·H$_2$O--.
Column 24, line 21, "HOBT-H$_2$O" should read --HOBT·H$_2$O--.
Column 24, line 66, "(Carboxycarbonyl)" should read --(t-butoxycarbonyl)--.
Column 25, line 5, "HOBT" should read --HOBT·--.

UNITED STATES PATENT AND TRADEMARK OFFICE
CERTIFICATE OF CORRECTION

PATENT NO. : 5,554,653

DATED : September 10, 1996

INVENTOR(S) : Hui, et al

It is certified that error appears in the above-identified patent and that said Letters Patent is hereby corrected as shown below:

Column 25, line 66, "$C_{32}H^{41}N_3O_6S.0.5H_2O$:" should read --$C_{32}H_{41}N_3O_6S·0.5H_2O$:--.
Column 26, line 10, "$HOBT-H_2O$" should read --$HOBT·H_2O$--.
Column 26, line 67, "$C_{36}H_{41}N_3O_6S\ 1.7H_2O$:" should read --$C_{36}H_{41}N_3O_6S·1.7H_2O$:--.
Column 27, line 19, "(hr. s, 1H)," should read --(br.s, 1H),--.
Column 27, line 37, first occurrence of "1H," should read --1H),--.
Column 27, line 38, "2H," should read --2H),--.
Column 27, line 54, "$HOBT.H_2O$" should read --$HOBT·H_2O$--.
Column 27, line 61, "1H)" should read --1H),--.
Column 28, line 14, "$C_{35}H_{41}N_3O_7S_2.1.5H_2O$:" should read --$C_{35}H_{41}N_3O_7S_2·1.5H_2O$:--.
Column 28, line 27, "$HOBT.H_2O$" should read --$HOBT·H_2O$--.
Column 28, line 45, "$C_{31}HB_{39}N_3O_3S$:" should read --$C_{31}H_{39}N_3O_3S$:--.
Column 28, line 64, "62;82;" should read --62.82;--.
Column 29, line 30, "$HOBT.H_2O$" should read --$HOBT·H_2O$--.
Column 30, line 1, "$HOBT.H_2O$" should read --$HOBT·H_2O$--.
Column 30, line 17, "$HOBT.H_2O$" should read --$HOBT·H_2O$--.
Column 31, line 1, "{q," should read --(q,--.
Column 31, line 1, "{t," should read --(t,--.
Column 31, line 16, "$HOBT.H_2O$" should read --$HOBT·H_2O$--.
Column 32, line 5, "1.42" should read --$\delta 1.42$--.
Column 32, line 8, "(m," should read --(m,--.
Column 33, line 6, "$HOBT.H_2O$" should read --$HOBT·H_2O$--.
Column 33, line 9, "$^1NMR$" should read --$^1H\ NMR$--.
Column 33, line 26, "$HOBT.H_2O$" should read --$HOBT·H_2O$--.
Column 33, line 40, "$HOBT.H_2O$" should read --$HOBT·H_2O$--.
Column 34, line 33, "$HOBT.H_2O$" should read --$HOBT·H_2O$--.
Column 34, line 53, "($M_{+1}$)." should read --($M^{+1}$).--.
Column 34, line 61, "(0.20 mmol)" should read --(0.20 mmol)--.
Column 35, line 36, "$HOBT.H_2O$" should read --$HOBT·H_2O$--.
Column 37, line 5, "NMH" should read --NMM--.
Column 37, line 44, "$HOBT.H_2O$" should read --$HOBT·H_2O$--.

UNITED STATES PATENT AND TRADEMARK OFFICE
CERTIFICATE OF CORRECTION

PATENT NO. : 5,554,653
DATED : September 10, 1996
INVENTOR(S) : Hui, et al

It is certified that error appears in the above-identified patent and that said Letters Patent is hereby corrected as shown below:

Column 38, line 47, "HOBT.H₂O" should read --HOBT·H₂O--.
Column 39, line 9, "4ylsulfinyl]" should read --4-ylsulfinyl]--.
Column 39, line 33, "HOBT.H₂O" should read --HOBT·H₂O--.
Column 40, line 16, "HOBT.H₂O" should read --HOBT·H₂O--.
Column 42, line 28, "Propellane 2           70.00 " should read --Propellant 22--.
Column 43, line 59, "Isotonic soline        1,000 mL" should read --Isotonic saline     1,000 mL--.
Column 46, line 25, "Set. 0.96;" should read --Ser. 0.96;--.
Column 46, line 54, "Ash" should read --Asn--.
Column 47, line 22, "GlY" should read --Gly--.

Column 53, line 67, "-N-8-butyl-" should read -- -N-t-butyl- --.
Column 54, line 10, "7-quinotin-2" should read --7-quinolin-2--.

Signed and Sealed this

Tenth Day of November 1998

Attest:

BRUCE LEHMAN

Attesting Officer     Commissioner of Patents and Trademarks